US007442499B2

United States Patent
Brown et al.

(10) Patent No.: US 7,442,499 B2
(45) Date of Patent: *Oct. 28, 2008

(54) SUBSTRATES COMPRISING POLYNUCLEOTIDE MICROARRAYS

(75) Inventors: Patrick O. Brown, Stanford, CA (US); Tidhar Dari Shalon, Los Cerros, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/356,322

(22) Filed: Nov. 24, 1998

(65) Prior Publication Data

US 2003/0012695 A1 Jan. 16, 2003

Related U.S. Application Data

(63) Continuation of application No. 08/688,488, filed on Jul. 30, 1996, now Pat. No. 7,323,298, which is a continuation-in-part of application No. 08/514,875, filed on Aug. 14, 1995, now Pat. No. 7,378,236, which is a continuation-in-part of application No. 08/477,809, filed on Jun. 7, 1995, now Pat. No. 5,807,522, which is a continuation-in-part of application No. 08/261,388, filed on Jun. 17, 1994, now abandoned.

(51) Int. Cl.
*C12Q 1/68* (2006.01)
*C12M 1/36* (2006.01)
*C07H 21/04* (2006.01)

(52) U.S. Cl. .................. 435/6; 435/174; 435/283.1; 435/287.2; 422/68.1; 536/23.1

(58) Field of Classification Search ............... 435/6, 435/69.1, 91.1, 91.2; 422/50, 68.1
See application file for complete search history.

(56) References Cited

U.S. PATENT DOCUMENTS 3,077,780 A 2/1963 Takatsy .................. 73/425.4

(Continued)

FOREIGN PATENT DOCUMENTS

CA 1284931 6/1991

(Continued)

OTHER PUBLICATIONS

Augenlicht et al., "*Cloning and Screening of Sequences Expressed in a Mouse Colon Tumor,*" Cancer Research, 42, 1088-1093 (1982).

(Continued)

*Primary Examiner*—BJ Forman
(74) *Attorney, Agent, or Firm*—Howrey LLP

(57) ABSTRACT

A method of determining the relative amounts of individual polynucleotides in a complex mixture of different-sequence polynucleotides is disclosed. The polynucleotides, after fluorescent labeling, are contacted under hybridization conditions with an array of different DNA sequences disposed at discrete locations on a non-porous surface, at an array density of at least about 100 sequences/cm$^2$, where the different DNA sequences in the array are effective to hybridize to individual polynucleotides in the mixture. The level of fluorescence associated with each array sequence provides a measure of its relative amount in the mixture.

20 Claims, 9 Drawing Sheets
(7 of 9 Drawing Sheet(s) Filed in Color)

U.S. PATENT DOCUMENTS

| | | | |
|---|---|---|---|
| 3,615,240 A | 10/1971 | Sanz | 23/259 |
| 3,730,844 A | 5/1973 | Gilham et al. | 195/103.5 R |
| 3,849,137 A | 11/1974 | Barzynski et al. | |
| 4,071,315 A | 1/1978 | Chateau | 23/230 B |
| 4,121,222 A | 10/1978 | Diebold et al. | 346/75 |
| 4,162,896 A | 7/1979 | Hosli | 23/230 R |
| 4,216,245 A | 8/1980 | Johnson | 427/2 |
| 4,269,933 A | 5/1981 | Pazos | |
| 4,325,913 A | 4/1982 | Wardlaw | 422/100 |
| 4,327,073 A | 4/1982 | Huang | 424/1 |
| 4,340,390 A | 7/1982 | Collins et al. | 23/230 B |
| 4,378,333 A | 3/1983 | Laipply | 422/100 |
| 4,395,486 A | 7/1983 | Wilson et al. | 435/6 |
| 4,483,920 A | 11/1984 | Gillespie et al. | 435/6 |
| 4,486,539 A | 12/1984 | Ranki et al. | 436/504 |
| 4,516,833 A | 5/1985 | Fusek | |
| 4,517,338 A | 5/1985 | Urdea et al. | |
| 4,537,861 A | 8/1985 | Elings et al. | 436/518 |
| 4,542,102 A | 9/1985 | Dattagupta et al. | 435/6 |
| 4,556,643 A | 12/1985 | Paau et al. | 436/501 |
| 4,562,157 A | 12/1985 | Lowe et al. | 435/291 |
| 4,563,419 A | 1/1986 | Ranki et al. | 435/6 |
| 4,584,277 A | 4/1986 | Ullman | 436/501 |
| 4,586,546 A | 5/1986 | Mezei et al. | 141/2 |
| 4,588,682 A | 5/1986 | Groet et al. | 435/6 |
| 4,591,570 A | 5/1986 | Chang | 436/518 |
| 4,598,049 A | 7/1986 | Zelinka et al. | 435/287 |
| 4,613,566 A | 9/1986 | Potter | 435/6 |
| 4,631,211 A | 12/1986 | Houghten | 428/35 |
| 4,656,007 A | 4/1987 | Douchy et al. | 422/64 |
| 4,656,127 A | 4/1987 | Mundy | 435/6 |
| 4,668,476 A | 5/1987 | Bridgham et al. | 422/62 |
| 4,670,380 A | 6/1987 | Dattagupta | 435/6 |
| 4,675,301 A | 6/1987 | Charneski et al. | 436/180 |
| 4,677,054 A | 6/1987 | White et al. | 435/6 |
| 4,683,195 A | 7/1987 | Mullis et al. | 435/6 |
| 4,683,202 A | 7/1987 | Mullis | 435/91 |
| 4,689,405 A | 8/1987 | Frank et al. | 536/27 |
| 4,704,256 A | 11/1987 | Hood et al. | 422/68 |
| 4,704,353 A | 11/1987 | Humphries et al. | 435/4 |
| 4,711,955 A | 12/1987 | Ward et al. | 536/29 |
| 4,713,326 A | 12/1987 | Dattagupta et al. | |
| 4,715,413 A | 12/1987 | Backlund et al. | 141/94 |
| 4,716,106 A | 12/1987 | Chiswell | 435/6 |
| 4,728,502 A | 3/1988 | Hamill | |
| 4,728,591 A | 3/1988 | Clark et al. | 430/5 |
| 4,731,325 A | 3/1988 | Palva et al. | 435/6 |
| 4,737,344 A | 4/1988 | Koizumi et al. | 422/100 |
| 4,738,669 A | 4/1988 | Vlock | 604/289 |
| 4,746,490 A | 5/1988 | Saneii | 422/62 |
| 4,755,458 A | 7/1988 | Rabbani et al. | 435/5 |
| 4,757,437 A | 7/1988 | Nishimura | 364/167 |
| 4,762,881 A | 8/1988 | Kauer | |
| 4,766,062 A | 8/1988 | Diamond et al. | 435/6 |
| 4,767,700 A | 8/1988 | Wallace | 435/6 |
| 4,798,706 A | 1/1989 | Brigati | 422/102 |
| 4,811,062 A | 3/1989 | Tabata et al. | |
| 4,811,218 A | 3/1989 | Hunkapiller et al. | 364/413.01 |
| 4,818,492 A | 4/1989 | Shimizu | 422/100 |
| 4,820,630 A | 4/1989 | Taub | 435/5 |
| 4,833,092 A | 5/1989 | Geysen | 436/501 |
| 4,846,552 A | 7/1989 | Vekdkamp et al. | |
| 4,849,513 A | 7/1989 | Smith et al. | 536/27 |
| 4,855,225 A | 8/1989 | Fung et al. | 435/6 |
| 4,861,866 A | 8/1989 | Durrum et al. | 530/333 |
| 4,868,103 A | 9/1989 | Stavrianopoulos et al. | 435/5 |
| 4,868,104 A | 9/1989 | Kurn et al. | 435/6 |
| 4,868,105 A | 9/1989 | Urdea et al. | 435/6 |
| 4,874,500 A | 10/1989 | Madou et al. | 204/412 |
| 4,877,745 A | 10/1989 | Hayes et al. | |
| 4,886,741 A | 12/1989 | Schwartz | 435/5 |
| 4,888,278 A | 12/1989 | Singer et al. | 435/6 |
| 4,921,805 A | 5/1990 | Gebeyehu et al. | 435/270 |
| 4,923,901 A | 5/1990 | Koester et al. | 521/53 |
| 4,925,785 A | 5/1990 | Wang et al. | 435/6 |
| 4,931,384 A | 6/1990 | Layton et al. | 435/7 |
| 4,944,922 A | 7/1990 | Hayashi | 422/100 |
| 4,946,942 A | 8/1990 | Fuller et al. | |
| 4,965,188 A | 10/1990 | Mullis et al. | 435/6 |
| 4,973,493 A | 11/1990 | Guire | 427/2 |
| 4,981,783 A | 1/1991 | Augenlicht | 435/6 |
| 4,981,985 A | 1/1991 | Kaplan et al. | |
| 4,984,100 A | 1/1991 | Takayama et al. | |
| 4,987,065 A | 1/1991 | Stavrianopoulos et al. | 435/5 |
| 4,988,617 A | 1/1991 | Landegren et al. | 435/6 |
| 4,994,373 A | 2/1991 | Stavrianopoulos et al. | 435/6 |
| 5,002,867 A | 3/1991 | Macevicz | 435/6 |
| 5,006,464 A | 4/1991 | Chu et al. | 435/7.1 |
| 5,011,770 A | 4/1991 | Kung et al. | 435/6 |
| 5,013,669 A | 5/1991 | Peters, Jr. et al. | 436/518 |
| 5,026,773 A | 6/1991 | Steel | 525/54.11 |
| 5,026,840 A | 6/1991 | Dattagupta et al. | 536/27 |
| 5,028,525 A | 7/1991 | Gray et al. | 435/6 |
| 5,028,545 A | 7/1991 | Soini | 436/501 |
| 5,037,882 A | 8/1991 | Steel | 525/54.11 |
| 5,043,265 A | 8/1991 | Tanke et al. | 435/6 |
| 5,059,398 A | 10/1991 | Kenney | 422/100 |
| 5,063,081 A | 11/1991 | Cozzette et al. | 427/2 |
| 5,064,754 A | 11/1991 | Mills | 435/6 |
| 5,077,085 A | 12/1991 | Schnur et al. | 427/98 |
| 5,077,210 A | 12/1991 | Eigler et al. | 435/176 |
| 5,079,600 A | 1/1992 | Schnur et al. | 357/4 |
| 5,082,830 A | 1/1992 | Brakel et al. | 514/44 |
| 5,091,652 A | 2/1992 | Mathies et al. | 250/458.1 |
| 5,094,594 A | 3/1992 | Brennan | 417/322 |
| 5,096,807 A | 3/1992 | Leaback | 435/6 |
| 5,100,626 A | 3/1992 | Levin | 422/100 |
| 5,100,777 A | 3/1992 | Chang | 435/7.24 |
| 5,143,849 A | 9/1992 | Barry et al. | 436/50 |
| 5,143,854 A | 9/1992 | Pirrung et al. | 436/518 |
| 5,164,319 A | 11/1992 | Hafeman et al. | 435/291 |
| 5,171,695 A | 12/1992 | Ekins | 436/501 |
| 5,175,209 A | 12/1992 | Beattie et al. | 525/54.11 |
| 5,185,243 A | 2/1993 | Ullman et al. | 435/6 |
| 5,188,963 A | 2/1993 | Stapleton | 435/299 |
| 5,200,051 A | 4/1993 | Cozzette et al. | 204/403 |
| 5,200,312 A | 4/1993 | Oprandy | 435/5 |
| 5,202,231 A | 4/1993 | Drmanac et al. | 435/6 |
| 5,204,268 A | 4/1993 | Matsumoto | 436/44 |
| 5,215,882 A | 6/1993 | Bahl et al. | 435/6 |
| 5,219,726 A | 6/1993 | Evans | 435/6 |
| 5,225,326 A | 7/1993 | Bresser et al. | 435/6 |
| 5,232,829 A | 8/1993 | Longiaru et al. | 435/6 |
| 5,242,974 A | 9/1993 | Holmes | 525/54.11 |
| 5,252,296 A | 10/1993 | Zuckermann et al. | 422/116 |
| 5,252,743 A * | 10/1993 | Barrett et al. | 548/303.7 |
| 5,258,506 A | 11/1993 | Urdea et al. | |
| 5,324,633 A | 6/1994 | Fodor et al. | 435/6 |
| 5,328,824 A | 7/1994 | Ward et al. | 435/6 |
| 5,338,688 A | 8/1994 | Deeg et al. | 436/180 |
| 5,348,855 A | 9/1994 | Dattagupta et al. | 435/6 |
| 5,389,512 A | 2/1995 | Sninksy et al. | 435/5 |
| 5,412,087 A | 5/1995 | McGall et al. | 536/24.3 |
| 5,424,188 A | 6/1995 | Schneider et al. | 435/6 |
| 5,432,099 A | 7/1995 | Ekins | 436/518 |
| 5,434,049 A | 7/1995 | Okano et al. | 435/6 |
| 5,436,327 A | 7/1995 | Southern et al. | 536/25.34 |
| 5,445,934 A | 8/1995 | Fodor et al. | 435/6 |
| 5,447,841 A | 9/1995 | Gray et al. | 435/6 |
| 5,451,683 A | 9/1995 | Barrett et al. | |
| 5,455,008 A | 10/1995 | Earley et al. | 422/100 |
| 5,465,629 A | 11/1995 | Waylett, Jr. | 73/864.24 |
| 5,472,842 A | 12/1995 | Stokke et al. | 435/6 |
| 5,474,796 A | 12/1995 | Brennan | 427/2.13 |

| | | | |
|---|---|---|---|
| 5,474,895 A | 12/1995 | Ishii et al. ..................... 435/6 |
| 5,486,452 A | 1/1996 | Gordon et al. ................. 435/5 |
| 5,489,507 A | 2/1996 | Chehab ......................... 435/6 |
| 5,492,806 A | 2/1996 | Drmanac et al. ............... 435/5 |
| 5,510,270 A | 4/1996 | Fodor et al. ................. 436/518 |
| 5,512,430 A | 4/1996 | Gong ............................ 435/5 |
| 5,514,543 A | 5/1996 | Grossman et al. ............. 435/6 |
| 5,514,785 A | 5/1996 | Van Ness et al. ......... 536/22.1 |
| 5,516,641 A | 5/1996 | Ullman et al. ................. 435/6 |
| 5,518,883 A | 5/1996 | Soini ............................ 435/6 |
| 5,525,464 A | 6/1996 | Drmanac et al. ............... 435/6 |
| 5,532,128 A | 7/1996 | Eggers et al. ................ 435/16 |
| 5,545,531 A | 8/1996 | Rava et al. .................... 435/6 |
| 5,556,748 A | 9/1996 | Douglas ........................ 435/6 |
| 5,556,752 A | 9/1996 | Lockhart et al. ............... 435/6 |
| 5,563,060 A | 10/1996 | Hozier .................. 435/240.23 |
| 5,569,584 A | 10/1996 | Augenlicht .................... 435/6 |
| 5,578,832 A | 11/1996 | Trulson et al. ........... 250/458.1 |
| 5,599,720 A | 2/1997 | Ekins ........................ 436/501 |
| 5,604,099 A | 2/1997 | Erlich et al. ................... 435/6 |
| 5,605,662 A | 2/1997 | Heller et al. ............... 422/68.1 |
| 5,665,549 A | 9/1997 | Pinkel et al. ................... 435/6 |
| 5,677,195 A | 10/1997 | Winkler et al. ............. 436/518 |
| 5,695,940 A | 12/1997 | Drmanac et al. ............... 435/6 |
| 5,700,637 A | 12/1997 | Southern ....................... 435/6 |
| 5,723,320 A * | 3/1998 | Dehlinger .................. 435/91.1 |
| 5,744,305 A * | 4/1998 | Fodor et al. .................... 435/6 |
| 5,763,262 A | 6/1998 | Wong et al. .............. 435/287.2 |
| 5,795,716 A | 8/1998 | Chee et al. ..................... 435/6 |
| 5,800,992 A | 9/1998 | Fodor et al. .................... 435/6 |
| 5,807,522 A * | 9/1998 | Brown et al. ................... 422/50 |
| 5,830,645 A * | 11/1998 | Pinkel et al. ................... 435/6 |
| 5,869,237 A | 2/1999 | Ward et al. ..................... 435/6 |
| 5,985,551 A | 11/1999 | Brennan ........................ 435/6 |
| 6,013,440 A * | 1/2000 | Lipshutz et al. ................ 435/6 |
| 6,013,449 A | 1/2000 | Hacia et al. |
| 6,040,166 A | 3/2000 | Erlich et al. ................. 435/194 |
| 6,040,193 A | 3/2000 | Winkler et al. .............. 436/180 |
| 6,045,996 A | 4/2000 | Cronin et al. |
| 6,171,843 B1 | 1/2001 | Bandman et al. |

FOREIGN PATENT DOCUMENTS

| | | |
|---|---|---|
| EP | 0046083 A2 | 2/1982 |
| EP | 0 063 810 A1 | 11/1982 |
| EP | 0103197 A1 | 3/1984 |
| EP | 0 130 523 A2 | 1/1985 |
| EP | 0130739 A2 | 1/1985 |
| EP | 0 142 299 A2 | 5/1985 |
| EP | 0142299 A2 | 5/1985 |
| EP | 0 171 150 A2 | 2/1986 |
| EP | 0 171 150 B1 | 2/1986 |
| EP | 0 185 547 A2 | 6/1986 |
| EP | 0 194 132 A2 | 9/1986 |
| EP | 0194132 A2 | 9/1986 |
| EP | 0 228 075 A2 | 7/1987 |
| EP | 0228075 A2 | 7/1987 |
| EP | 0 235 726 A2 | 9/1987 |
| EP | 0 237 362 A1 | 9/1987 |
| EP | 0237362 A1 | 9/1987 |
| EP | 0238332 A2 | 9/1987 |
| EP | 0 260 965 A2 | 3/1988 |
| EP | 0 268 237 A2 | 5/1988 |
| EP | 0268237 A2 | 5/1988 |
| EP | 0 281 927 A2 | 9/1988 |
| EP | 0 304 202 B1 | 2/1989 |
| EP | 0 328 256 A1 | 8/1989 |
| EP | 0328256 A1 | 8/1989 |
| EP | 0 337 498 A2 | 10/1989 |
| EP | 0 337 498 A3 | 10/1989 |
| EP | 0 373 203 A | 6/1990 |
| EP | 0 392 546 A2 | 10/1990 |
| EP | 0392546 A2 | 10/1990 |
| EP | 0173 339 B1 | 1/1992 |
| EP | 0 185 547 B1 | 6/1992 |
| EP | 0 232 967 B1 | 4/1993 |
| EP | 0 535 242 A1 | 4/1993 |
| EP | 0717113 A2 | 6/1996 |
| EP | 721016 A2 | 7/1996 |
| GB | 2 156 074 A | 10/1985 |
| GB | 2156074 A | 10/1985 |
| GB | 2196476 A | 4/1988 |
| GB | 2248840 | 6/1990 |
| JP | 59-24244 | 2/1984 |
| JP | 62-254034 | 11/1987 |
| JP | 63-223557 | 9/1988 |
| WO | WO 84/03151 | 8/1984 |
| WO | WO 85/01051 | 3/1985 |
| WO | WO 86/00991 | 2/1986 |
| WO | WO 86/06487 | 11/1986 |
| WO | WO 86/06487 A1 | 11/1986 |
| WO | WO 88/01058 A1 | 2/1988 |
| WO | WO 88/01302 A1 | 2/1988 |
| WO | WO 89/10977 | 5/1989 |
| WO | WO 89/11548 | 11/1989 |
| WO | WO 90/00626 A1 | 1/1990 |
| WO | WO 90/02605 A1 | 3/1990 |
| WO | WO 90/03382 | 4/1990 |
| WO | WO 90/04652 | 5/1990 |
| WO | WO 90/05789 | 5/1990 |
| WO | WO 90/07582 A1 | 7/1990 |
| WO | WO 90/15070 | 12/1990 |
| WO | WO 91/00511 A1 | 1/1991 |
| WO | WO 91/00868 A1 | 1/1991 |
| WO | WO 91/07087 A1 | 5/1991 |
| WO | WO 92/10092 A1 | 6/1992 |
| WO | WO 92/10588 | 6/1992 |
| WO | WO 93/09668 | 5/1993 |
| WO | WO 93/17126 A1 | 9/1993 |
| WO | WO 93/18186 | 9/1993 |
| WO | WO 93/22680 | 11/1993 |
| WO | WO 95/00530 | 1/1995 |
| WO | WO 95/11755 A1 | 5/1995 |
| WO | WO 95/11995 | 5/1995 |
| WO | WO 95/15970 | 6/1995 |
| WO | WO 95/21944 | 8/1995 |
| WO | WO 95/25116 | 9/1995 |
| WO | WO 96/17958 | 6/1996 |
| WO | WO 97/10365 | 3/1997 |
| YU | 18617/87-P-570/87 | 2/1988 |
| YU | P-570/87 | 2/1988 |

OTHER PUBLICATIONS

Angenlicht et al., "*Expression of Cloned Sequences in Biopsies of Human Colonic Tissue and in Colonic Carcinoma Cells Induced to Differentiate in Vitro,*" Cancer Research 47, 6017-6021 (1987).

W. Bains and G. Smith, "*A Novel Method for Nucleic Acid Sequence Determination,*" Theor. Biol. 135: 303-307 (1988).

Bartsch et al., "*Cloning of mRNA Sequences from the Human Colon: Preliminary Characterisation of Defined mRNAs in Normal and Neoplastic Tissues,*" Br. J. Cancer, 54:791-798 (1986).

Boyle et al., "*Differential Distribution of Long and Short Interspersed Element Sequences in the Mouse Genome: Chromosome Karvotypina by Fluorescence in situ Hybridization,*" 87:7757-7761 (1990).

Brock et al., "*Rapid Fluorescence Detection of in Situ Hybridization with Biotinylated Bovine Herpesvirus-1 DNA Probes,*" J Vet Diagn. Invest, I:34-38 (1989).

Carrano et al. "*A High-Resolution, Fluorescence-Based, Semiautomated Method for DNA Fingerprinting,*" Genomics 4, 129-136 (1989).

Caruthers, "*Gene Synthesis Machines: DNA Chemistry and Its Uses,*" Science, 230:281 (1985).

F. Chehab & Y. W. Kan, "*Detection of Specific DNA sequences by fluorescence Amplification: A Color Complementation Assay,*" Proc. Natl. Acad. Sci. USA, vol. 86, p. 9178-9182 (1989).

Chehab et al., "*Detection of Sickle Cell Anaemia Mutation by Colour DNA Amplification,*" The Lancet 335:15-17 (1990).

Craig et al. "*Ordering of Cosmid Clones Covering the Herpes Simplex,*" Virus Type I (HSV-I) Genome, Nuc. Acids. Res. 18:2653-2660 (1990).

Drmanac et al., "*Sequencing of Megabase Plus DNA by Hybridization: Theory of the Method,*" Genomics, 4:114-128 (1989).

Drmanac et al., "*Sequencing By Oligonucleotide Hybridization: A Promising Framework In Decoding of the Genome Program?*" in The First Intl. Conf. Electrophoresis. Supercomputing and the Human Genome, Eds. Cantor and Lim, World Scientific, pp. 47-59. (1990).

Drmanac et al., "*Partial Sequencing By Oligo-Hybridization: Concepts and Applications in Genome Analysis*" in The First Intl. Conf. Electrophoresis. Supercomputing and the Human Genome. Eds. Cantor and Lim, World Scientific pp. 60-74. (1990).

Ekins et al., *Development of Microspot Multi-Analyte Ratiometric Immunoassay Using Dual Fluorescent-Labelled Antibodies.* Analytica Chimica Acta 227: 73-96 (1989).

Ekins et al., "*Fluorescence Spectroscopy and its Application to a New Generation of High Sensitivity, Multi-Microspot, Multianalyte, Immunoassay,*" Clinica Chimica Acta 194:91-114 (1990).

Evans et al., "*Physical Mapping of Complex Genomes by Cosmid Multiplex Analysis,*" Proc. Natl. Acad Sci USA, 86:5030-5034 (1989).

Ezaki et al., "*Small-Scale DNA Preparation for Rapid Genetic Identification of Campylobacter Species without Radioisotope*", Microbiol. Immunol., 32:141-150 (1988).

Fan et al., "*Mapping Small DNA Sequences by Fluorescence in situ Hybridization Directly on Banded Metaphase Chromosomes,*" Proc. Natl. Acad. Sci. USA 87:6223-6227 (1990).

Frank et al., "*Simultaneous Synthesis and Biological Applications of DNA Fragments: An Efficient and Complete Methodolgy,*" Methods in Enzymology 134:221-251 (1987).

Gait et al., "*Olizonucleotide Synthesis: A Practical Approach,*" (IRL Press, London, 1984).

Gergen et al., "*Filter Replicas and Permanent Collections of Recombination DNA Plasmids.*" Nucleic Acids Res. 7:2115-2135 (1979).

Gumerlock et al., "*RAS Enzyme-Linked Immunoblot Assay Discriminates p21Species: A Technique to Dissect Gene Family Expression,*" Analytical Biochemistry, 180:158-68 (1989).

Haase et al., "*Detection of Two Viral Genomes in Single Cells by Double-Label Hybridization in Situ and Color Microradioautoerapy,*" Science, vol. 227 p. 189-191 (1985).

D. Hanahan and M. Meselson, "*Plasmid Screening at High Colony Density,*" Gene 10:63-67(1980).

D. Hanahan and M. Meselson., "*Plasmid Screening at High Colony Density,*" Methods in Enzymology, vol. 100:333-347 (1983).

Hopman et al., "*Bi-Color Detection of Two Target DNAs by Non-Radioactive in situ Hybridization,*" Histochemistry, 85: 1-4 (1986).

P. Kerkof and G. Kelly, "*A Procedure for Making Simultaneous Determinations of the Relative Levels of Gene Transcripts in Tissues or Cells,*" Anal. Biochem., 188: 349-355 (1990).

Khrapko, et al., "*An Oligonucleotide Hybridization Approach to DNA Sequencing,*" FEB 07689 256:118-122 (1989).

Kievits et al., "*Rapid Subchromosomal Localization of Cosmids by Nonradioactive in situ Hybridization,*" Cytogenet Cell Genet 53:134-136 (1990).

Kimura et al., "*An Immobilized Enzyme Membrane Fabrication Method Using an Ink Jet Nozzle,*" Biosensors 40:41-52 (1988).

Kitazawa et al., "*In situ DNA-RNA hybridization Using in Vivo Bromodeoxyuridine-labeled DNA probe,*" Histochemistry 92:195-199 (1989).

Kleinfeld et al., "*Controlled Outgrowth of Dissociated Neurons on Patterned Substrates,*" The Journal of Neuroscience 8:4098-4120 (1988).

Kohara et al., "*The Physical Map of the Whole E. coli Chromosome: Application of a New Strategy for Rapid Analysis and Sorting of a Large Genomic Library,*" Cell 50:495-508 (1987).

Lanier et al., "*Human* Lymphocyte Subpopulations Identified by Using Three-Color Immunofluorescence and Flow Cytometry Analysis", The Journal of Immunology, 132:151-156 (1984).

Laurence et al., "*Messenger RNA Prevalence in Sea Urchin Embryos Measured with Cloned cDNA's,*" Proc. Natl. Acad. Sci., 77:5317-5321 (1986).

Lichter et al., "*Rapid Detection of Human Chromosome 21 Aberrations By in situ Hybridization,*" Proc. Natl. Acad. Sci. USA 85:9664-9668 (1988).

Lichter et al., "*Fluorescence In Situ* Hybridization with Alu and L1 Polvmerase Chain Reaction Probes for Rapid Characterization of Human Chromosomes in Hybrid Cell Lines," Proc. Natl. Acad. Sci. USA 87:6634-6638 (1990).

Lichter et al., "*High-Resolution Mapping of Human Chromosome 11 by in Situ Hvbridization with Cosmid Clones,*" Science, vol. 247 (1990).

P. Lichter and D.C. Ward, "*Is Non-Isotopic in situ Hybridization Finally coming of Age?*" Nature, 345: 93-94 (1990).

Loken et al., "*Three Color Immunofluorescence Analysis of Leu Antigens on Human Peripheral Blood Using Two Lasers on a Fluorescence-Activated Cell Sorter,*" Cytometry 5: 151-158 (1984).

Love et al., "*Screening of Lambda Library for Differentially Expressed Genes Using in Vitro Transcipts,*" Anal Biochem, 150:429-41 (1985).

Lu et al., "*Differential Screening of Murine Ascites cDNA Libraries by Means of In Vitro Transcripts of Cell-Cycle-Phase-Specific cDNA and Digital Image Processing,*" Gene 86:185-92 (1990).

Lysov et al., "*A New Method for Determining the DNA Nucleotide Sequence By Hvbridization With Oligonucleotides,*" Doklady Biochemistry 303:355-452 (1988).

Lysov, "*DNA Sequencing By Oligonucleotide Hybridization,*" in The First Intl. Conf. Electrophoresis Supercomputing, and the Human Genome, Eds. Cantor and Lim, World Scientific, pp. 157-163 (Apr. 1990).

Masiakowski et al., "*Cloning of cDNA Sequences of Hormone-Regulated Genes from the MCF-7 Human Breast Cancer Cell Line,*" Nucleic Acids Research, 10:7895-7903 (1982).

J. Meinkoth and G. Wahl, "*Hybridization of Nucleic Acids Immobilized on Solid Supports,*" Analytical Biochemistry 138, 267-284 (1984).

Michiels et al., "*Molecular Approaches0 to Genome Anaylsis: A Strategy for the Construction of Ordered Overlapping Clone Libraries*" CABIOS, vol. 3, No. 3, p. 203-210 (1987).

Morrison et al., "*Solution-Phase Detection of Polynucleotides Using Interacting Fluorescent Labels and Competitive Hybridization,*" Analytical Biochemistry, 183 :231-244 (1989).

Nakamori et al., "*A Simple and Useful Method for Simultaneous Screening of Elevated Levels of Expression of a Variety of Oncogenes in Malignant Cells,*"Jpn. J. Cancer Res. (Gann), 79:1311-1317 (1988).

Nederlof et al., "*Multiple Fluorescence In Situ Hvbridization,*" Cytometry I I:126-131 (1990).

Poustka et al., "*Molecular Approaches to Mammalian Genetics,*" Cold Spring Harbor Symposium on Quantitative Biology 51: 131-139 (1986).

Saiki et al., "*Genetic Analysis of amplified DNA with Immobilized Sequence-Specific Oligonucleotide Probes,*" Proc. Natl. Acad. Sci. USA, vol. 86, pp. 6230-6234 (1989).

Sim et al., "*Use of a cDNA Library for Studies on Evolution and Developmental Expression of the Chorion Multigene Families,*" Cell 18:1303-1316 (1979).

Stryer, *Biochemistrv—Third Edition,* (W.H. Freeman and Company, New York, 1988).

Thomas, "*Hybridization of Denatured RNA and Small DNA Fragments Transferred to Nitrocellulose,*" Proc. Natl. Acad. Sci. USA 77:5201-5205 (1980).

Titus et al., "*Texas Red, A Hydrophilic, Red-Emitting Fluorophore for Use Wtih Fluorescein in Dual Parameter Flow Microfluorometric and Fluorescence Microscopic Studies,*" Journal of Immunological Methods, 50:193-204 (1982).

Tkachuk et al., "*Detection of bcr-abl Fusion in Chronic Myelogenous Leukemia by in Situ Hybridization,*" Science, vol. 250, pp. 559 (1990).

Tsutsumi et al., "*Expression of L- and M- Type Pyruvate Kinase in Human Tissues,*" Genomics 2:86-9 (1988).

Turchinskii et al., "*Multiple Hybridization in Genome Analysis. The Reaction of Diamines and Bisulfite with Cytosine for Introduction of Nonradioactive Labels into DNA,*" Molekulyarnaya Biologiya (English Translation), 22: 1229-1235 (1988).

Urdea et al., "*A Novel Method for the Rapid Detection of Specific Nucleotide Sequences in Crude Biological Samples without Blotting or Radioactivity; Application to the Analysis of Hepatitis B Virus in Human Serum,*" Gene, 61 :253-264 (1987).

Urdea et al., "*A Comparison of Non-Radioisotopic Hybridization Assay Methods Using Fluorescent, Chemiluminescent and Enzyme Labeled Synthetic Oligodeoxyribonucleotides probes,*" Nuc. Acids, Res., 16: 4937-4956 (1988).

Wallace et al., "Hybridization of Synthetic Oligodeoxyribonucleotides to *x* 174 DNA: *the Effect of Single Base Pair Mismatch,*" Nucleic Acids Research, 11 :3543-3557 (1979).

Widacki et al., "*Biochemical Differences in Qa-2 Antigens Expressed by Qa- 2+, 6+ and Qa-2+, 6- Strains. Evidence for Differential Expression of the Q7 and Q9 Genes*" Mol. Immunol. 27:559-70 (1990).

Wu et al., "*Synthesis and Properties of Adenosine-5'-triphosphoro-y-l-(5-sulfonic acid) naphthyl Ethylamidate: A Fluorescent Nucleotide Substrate for DNA-Dependent RNA Polymerase from Escherichia coli,*" Arch Biochem. Biophys., 246:564-71 (1986).

Wu et al., "*Direct Analysis of Single Nucleotide Variation in Human DNA and RNA Using In Situ Dot Hybridization,*" DNA 8:135-142 (1989).

Yarbrough et al., "*Synthesis and Properties of Fluorescent Nucleotide Substrates for DNA—Dependent RNA Polymerases,*" J. Biol. Chem. 254: 12069-73 (1979).

Young, "*Simultaneous Use of Digoxigenin-and Radiolabeled Oligodeoxyribonucleotide Probes for Hybridizaion Histochemistry,*" Neuropeptides 13, 271-275 (1989).

Nederlof et al., "Three-Color Fluorescence In Situ Hybridization for the Simulatneous Detection of Multiple Nucleic Acid Sequences," *Cytometry*, 10:20-27 (1989).

M. Renz and C. Kurz, "A colorimetric method for DNA hybridization," *Nucleic Acids Research*, 12(8):3425-3445 (1984).

Hayakawa, Y., et al., "Allylic Protecting Groups in Solid Phase DNA Synthesis," *Nucl. Acids. Res.*, 20:75-76(1988).

Hayakawa, Y., et al., "The Allylic Protection Method in Solid-Phase Oligonucleotide Synthesis. An Efficient Preparation of Solid-Anchored DNA Oligomers," *J. Am. Chem. Soc.* 112:1691-1696 (1990).

Katzhendler, J., et al., "The Effect of Spacer, Linkage and Solid Support on the Synthesis of Oligonucleotides," *Tetrahedron*, 45(9):2777-2792 (1989).

Koster, H., et al., "N-Acyl Protecting Groups for Deoxynucleosides," *Tetrahedron*, 37:363-369(1981).

Pochert, S. et al., "Synthesis of DNA Fragments Linked to a Solid Support," *Tetrahedron*, 43(15):3481-3490(1987).

Schulhof, D., et al., "The Final Deprotection Step in Oligonucleotide Synthesis is Reduced to a Mild and Rapid Ammonia Treatment by Using Labile Base-protecting Groups," *Nucl. Acids. Res.*, 15(2):397-416(1987).

Southern, E.M.., et al., "Analysis and Comparing Nucleic Acid Sequences by Hybridization to Arrays of Oligonucleotides: Evaluation Using Experimental Models," *Genomics.*, 13:1008-1017(1992).

Sproat, B and D.M. Brown., "A New Linkage for solid phase synthesis of oligonucleotides," *Nucl. Acids. Res.*, 13(8): 2979-2987(1985).

"Drives help automate the Human Genome Project," *Design Engineering*, p. 31 (1994).

Ekins, R., and Chu, F., "Developing multianalyte assays," *Tibtech*, 12:89-94 (1994).

Ekins, R., et al., "High specific activity chemiluminescent and fluorescent markers: their potential application to high sensitivity and 'Multi-analyte'immunoassays", *Journal of Bioluminescence and Chemiluminescence*, 4:59-78 (1988)

Gress, T., et al., "Hybridization fingerprinting of high-density of cDNA-library arrays with cDNA pools derived from whole tissues", *Mammalian Genome*, 3:609-619(1992).

Khrapko, K.R., et al., "Hybridization of DNA with oligonucleotides immobilized in gel: a convenient method for detecting single base substitutions," *Molecular Biology*, 25(3):581-591 (1991).

Maier, E., et al., "Application of robotic technology to automated sequence fingerprint analysis by oligonucleotide hybridization," *Journal of Biotechnology*, 35:191-203 (1994).

Maier, E., et al., Hybridisation techniques on gridded high density DNA and in situ colony filters based on fluorescence detecton, *Nucleic Acids Research*, 22(16):3423-3434 (1994).

Meier-Ewert, S., et al., "Establishing catalogues of expressed sequences by oligonucleotide fingerprinting of cDNA libraries," *Identification of Transcribed Sequences*, 253-260 (1994).

Mirzabekov, A., "DNA sequencing by hybridization—a megasequencing method and a diagnostic tool?", *Tibtech*, 12:27-32 (1994).

Brennan, *Sequencing by Hybridization: Methods to Generate Large Arrays of Oligonucleotides*, Proposal by Genomyx for Department of Energy, Office of Energy Research Human Genome Grant (1991).

Ekins, *Developments In Immunoassay Methods*, Biochimica Clinica Suppl. 1-8:13 (1991).

Fodor, et al., *Multiplexed Biochemical Assays with Biological Chips* Nature 364:555-556 (1993).

Sproat and Brown, *A new linkage for solid phase synthesis of oligodeoxyribonucleotides*, Nucl. Acids. Res., 13(8):2979-2987 (1985).

Monaco, Lehrach et al., Abstract of paper presented at 1989 Meeting on Genome Sequencing and Mapping (Cold Spring Harbor Press) p. 90, Human Genome Linking with Cosmids and Yeast Artificial Chromosomes, Apr. 26, 1989.

Hoheisel, Lehrach et al., Adv. Mol. Gen. 4:125-132, Use of high coverage libraries for an integrated analysis of genomic DNA. 1991.

Meinkoth & Wahl, Anal. Biochem. 138:267-284, Hybridization of Nucleic Acids Immobilized on Sold Supports, 1984.

Dattagupta et al., Anal. Biochem. 177:85-89, Rapid Identification of Microorganisms by Nucleic Acid Hybridization after Labeling the Test Sample, 1989.

Kerkof & Kelly, Anal. Biochem. 188:349-355, A Procedure for Making Simultaneous Determinations of the Relative Levels of Gene Transcripts in Tissues or Cells, 1990.

Newman & Turner, Analytica ChImica Acta 262:13-17 (1992), Ink-jet printing for the fabrication of amperometric glucose biosensors, 1992.

Teng & Vest, Appl. Math. Modelling 12:182-188 (1988), Mathematical models of ink jet printing in thick-film hybrid microelectronics, Apr. 1988.

Kuriyama, Applied Biosensors (Donald Wise Ed.) Butterworths pp. 93-114 (1989), An ISFET Biosensor, 1989.

Frumgarts et al., Bioorg Khim, 12:1508-13 (1986), Preparation of fluorescent-labeled DNA and its use as a probe in molecular hybridization, 1986.

Uber et al., BioTechniques 11(5):642-647, Application of robotics and image processing to automated colony picking and arraying., Nov. 1991.

Ekins and Chu, Clin. Chem, 37(11):1955-1967, Multianalyte Microspot Immunoassay-Microanalytical 'Compact Disk' of the Future, 1991.

Bannwarth et al., DNA 5(5):413-419 (1986), Laboratory Methods: a System for the Simultaneous Chemical Synthesis of Different DNA Fragments on Solid Support, 1986.

Arnold et al., Federaton Proceedings 43(7) Abstract No. 3669 (1984), A Novel Universal Support for DNA & RNA Synthesis, 1984.

Takada et al., Fujitsu Sci. Tech. J. 22(2):132-138, Effect of Ink Channel Dimensions and Fluid Viscosity in Drop-on-Demand Ink-Jet Printing, Jun. 1986.

Hanahan & Meselson, Gene 10:63-67, Plasmid Screening at High Colony Density, 1980.

Lewin, Genes, John Wiley & Sons, New York, 1987.

Zischler, Epplen et al., Hum. Gen. 82:227-233, Digoxigenated oligonucleotide probes specific for simple repeats in DNA fingerprinting and hybridization in situ, 1989.

Teng & Vest, IEEE Trans. Indus. Elec. 35(3):407-412, A Microprocessor-Controlled Ink Jet Printing System for Electronic Circuits, Aug. 1988.

Bhatia et al., J. Am. Chem. Soc. 114:4432-4433, New Approach to Producing Patterned Biomolecular Assemblies, Feb. 1, 1992.

Kyser et al., J. Appl. Photographic Eng. 7(3):73-79 (1981), Design of an Impulse Ink Jet, Jun. 1981.

Wallace, J. Electronic Packaging 36(5):108-111, Automated Electronic Circuit Manufacturing Using Ink-Jet Technology, Jun. 1989.

Raoult and Dasch, J. Immunological Meth. 125:57-65, The Line Blot: an immunoassay for monoclonal and other antibodies, 1989

Hoheisel, Lehrach et al., J. Mol. Biol. 220:903-914 (1991), Use of High Coverage Reference Libraries of *Drosophila melanogaster* for Relational Data Analysis, Aug. 20, 1991.

Southern, J. Mol. Biol. 98:503-517 (1975), Detection of Specific Sequences Among DNA Fragments Separated by Gel Electrophoresis, Nov. 5, 1975.

Bernardini et al., J. Neuroscience Meth. 38:81-88, Applications of Piezoelectric Fluid Jetting Devices to Neuroscience Research, 1991.

Ekins, J. Pharm. Biomed. Anal. 7(2):155-168, Multi-analyte immunoassay, 1989.

Bains and Smith, J. Theor. Biol. 135:303-307 (1988), A Novel Method for Nucleic Acid Sequence Determination, 1988.

Longmire et al., LRA 3:195-198 (1991), Automated Construction of High-Density Gridded Arrays of Chromosome-Specific Cosmid Libraries, 1991.

Beltz et al., Meth. Enzymology 100(19):266-285, Isolation of Multigene Families and Determination of Homologies by Filter Hybridization Methods, 1983.

Hanahan & Meselson, Meth. Enzymology 100:333-342, Plasmid Screening at High Colony Density, 1983.

Miyada et al., Meth. Enzymology 154:94-107, Oligonucleotide Hybridization Techniques, 1987.

Kidd et al., Nature 304:230-234, alpha-1Antitrypsin deficiency detection by direct analysis of the mutation of the gene, Jul. 21, 1983.

Saiki et al., Nature 324:163-166, Analysis of Enzymatically Amplified B-Globin and HLA-DQa DNA With Allele-Specific Oligonucleotide Probes, Nov. 13, 1986.

Lichter and Ward, Nature 345:93-94, Is non-isotopic in situ hybridization finally coming of age?, May 3, 1990.

Little, Nature 346:611-612, Clone maps made simple, Aug. 16, 1990.

Ohtsuka et al., Nuc. Acids Res. 1(10):1351-1357, Studies on transfer ribonucleic acids and related compounds, Oct. 1974.

Seed, Nuc. Acids Res. 10(5):1799-1810, Diazotizable arylamine cellulose papers for the coupling and hybridization of nucleic acids, 1982.

Frank et al., Nuc. Acids Res. 11(13):4365-4377 (1983), A new general approach for the simultaneous chemical synthesis of large numbers of oligonucleotides: segmental solid supports, Jun. 8, 1983.

Renz & Kurz, Nuc. Acids Res. 12: 3435-3444, A colorimetric method for DNA hybridization, 1984.

Ghosh & Musso, Nuc. Acids Res. 15(13):5353-5372, Covalent attachment of oligonucleotides to solid supports, 1987.

Gingeras et al., Nuc. Acids Res. 15(13):5373-5390 (1987), Hybridization Properties of Immobilized Nucleic Acids, 1987.

Hodgson and Fisk, Nuc. Acids Res. 15(15):6295, Hybridization probe size control: optimized 'oligolabeling', 1987.

Schafer, Epplen et al., Nuc. Acids Res. 16(19):9344, DNA fingerprinting using non-radioactive oligonucleotide probes specific for simple repeats, 1988.

Zischler, Epplen et al., Nuc. Acids Res. 17(11):4411, Non-radioactive oligonucleotide fingerprinting in the gel, 1989.

Anand et al., Nuc. Acids Res. 18(8):1951-1956, A 3.5 genome equivalent multi access YAC library:construction, characterization, screening and storage, 1990.

Nizetic, Lehrach et al., Nuc. Acids Res. 19(1):182, An improved bacterial colony lysis procedure enables direct DNA hybridization using short (10, 11 bases) oligonucleotides to cosmids, Jan. 11, 1991.

Baxendale, Lehrach et al., Nuc. Acids Res. 19(23):6651, The direct screening of cosmid libraries with YAC clones, Dec. 11, 1991.

Maskos and Southern, Nuc. Acids Res. 20(7):1679-1684, Oligonucleotide hybridisations on glass supports, Mar. 9, 1992.

Kafatos et al., Nuc. Acids Res. 7(6):1541-1552, Determination of nucleic acid sequence homologies and relative concentrations by a dot hybridization procedure, Nov. 24, 1979.

Wallace et al., Nuc. Acids Res. 9(4):879-894, The use of synthetic Oligonucleotides as Hybridization Probes II: Hybridization of oligonucleotides of mixed sequence to rabbit b-globin DNA;, 1981.

Anderson & Young, Nucleic Acid Hybridisation: a pratical approach, ed. Hames, B.D., & Higgins, S.J., (IRL Press, Oxford) Chapter 4, Quantitative Filter Hybridisation.

Dattagupta et al., Perspectives in Antiinfective Therapy (Jackson et al., Eds. 1988) pp. 241-247, Nucleic Acid Hybridization: A Rapid Method for the Diagnosis of Infectious Diseases, Sep. 3, 1988.

Teng, Klen Fei Robert, Ph.D. Thesis 35372 Purdue University, Ink Jet Printing in Thick Film Hybrid Microelectronics, Dec. 19, 1986.

Ellis, Pharmaceutical Res. 3(4):195-207 (1986), The Applications of Synthetic Oligonucleotides to Molecular Biology, 1986.

Lasky et al., Proc. Nat'l. Acad. Sci. USA 77(9):5317-5321, Messenger RNA prevalence in sea urchin embryos measured with cloned cDNAs, Sep. 1986.

Wood et al., Proc. Nat'l. Acad. Sci. USA 82:1585-1588, Base composition-independent hybridization in tetramethlammonium chloride: a method for oligonucleotide screening of highly complex gene libraries, Mar. 1985.

Olson et al., Proc. Nat'l. Acad. Sci. USA 83:7826-7830, Randomclone strategy for genomic restriction mapping in yeast, Oct. 1986.

Strezoska, Drmanac, et al., Proc. Nat'l. Acad. Sci. USA 88:10089-10093, DNA sequencing by hybridization: 100 bases read by a nongel based method, Nov. 1991.

Nizetic, Lehrach et al., Proc. Nat'l. Acad. Sci. USA 88:3233-3237, Construction, Arraying and High Density Screening of Large Insert Libraries of Human Chromosomes X and 21, Apr. 1991.

Larin, Lehrach, et al., Proc. Nat'l. Acad. Sci. USA 88:4123-4127, Yeast artificial chromosome libraries containing large inserts from mouse and human DNA, May 1991.

Wallace et al., Proceedings, Bioprocess Eng. Symp. 1989 (Diller et al., eds.), Application of Ink-Jet Technology to Neuroscience Research and Biomedical Research, Dec. 1989.

Hayes & Wallace, Proceedings, ISHM '89, Application of Ink-Jet Technology to Microelectronic Packaging, Oct. 1989.

Abbott et al., Science 257:1380-1382, Manipulation of the Wettability of Surfaces on the 0.1-to 1-Micrometer Scale Through Micromachining and Molecular Self-Assembly, 1992.

Tonucci et al., Science 258:783-785, Nanochannel Array Glass, Oct. 30, 1992.

Bhatia et al., Sensors and Actuators B3:311-317, Immobilization of Acetylcholinesterase on Solid Surfaces: Chemistry and Activity Studies, 1991.

Ross et al., Techniques For The Analysis Of Complex Genomes Ch. 8 pp. 137-153, High Density Gridded YAC Filters: their Potential as Genome Mapping Tools, 1992.

Frank et al. Tetrahedron 44:6031-6040, Simultaneous Multiple Peptide Synthesis Under Continuous Flow Conditions on Cellulose Paper Discs as Segmental Solid Supports, 1988.

Matthes et al., The EMBO Journal 3(4):801-805 (1984), Simultaneous Rapid Chemical Synthesis of Over One Hundred Oligonucleotides on a Microscale, 1984.

Billings et al., "New Techniques for Physical Mapping of the Human Genome," *FASEB*, 5:28-34 (1991).

Chee, et al., "Accessing Genetic Information with High-Density DNA Arrays", *Science*, 274:610-614 (1996).

Drmanac et al., "DNA Sequence Determination by Hybridization: A Strategy for Efficient Large-Scale Sequencing," *Science*, 260:1649-1652 (1993).

Drmanac et al., "Laboratory Methods: Reliable Hybridization of Oligonucleotidesas Short as Six Nucleotides," *DNA and Cell Biology*, 9:527-534 (1990).

Drmanac et al., "Sequencing by Hybridization: Towards an Automated Sequencing of One Million M13 Clones Arrayed on Membranes," *Electrophoresis*, 13:566-573 (1992).

Ekins, et al., "Multianalyte Immunoassay: The Immunological 'Compact Disk' of the Future", *J. Clinical Immunoassay*, 13(4):169-181 (1990).

Fodor et al., "Light-Directed, Spatially Addressable Parallel Chemical Synthesis," *Science*, 251:767-773 (1991).

Guo, et al., "Direct Fluorescence Analysis of Genetic Polymorphisms by Hybridization with Oligonucleotide Arrays on Glass Supports", *Nucleic Acids Research*, 22:5456-5465 (1994).

Johnston, et al., "Chemistry of High Density Arrays: Factors Impacting Issues of Complexity", (Abstract) *Microbial & Comparative Genomics*, 1:235 (1996).

Kallioniemi et al., "Comparative Genomic Hybridization for Molecular Cytogenetic Analysis of Solid Tumors," *Science*, 258:818-821 (1992).

Kallioniemi et al., "Optimizing Comparative Genomic Hybridization for Analysis of DNA Sequence Copy Number Changes in Solid Tumors," *Genes, Chromosomes & Cancer*, 10:231-243 (1994).

Khrapko et al., "A Method for DNA Sequencing by Hybridization with Oligonucleotide Matrix," *DNA Sequencing and Mapping*1:375-388 (1991).

Kozal, et al., "Extensive Polymorphisms Observed in HIV-1 Clade B Protease Gene using High-Density Oligonucleotide Arrays", *Nature Medicine*, 2:753-759 (1996).

Kreiner, "Rapid Genetic Sequence Analysis Using a DNA Probe Array System," *American Laboratory* (March 1996).

Lehrach et al., "Hybridization Fingerprinting in Genome Mapping and Sequencing," in *Genome Analysis*, vol. I: Genetic and Physical Mapping. (K.E. Davies & S.M. Tilgham, Eds.) Cold Spring Harbor Laboratory Press, pp. 39-81 (1990).

Lennon et al., "Hybridization Analyses of Arrayed cDNA Libraries," *Trends In Genetics*, 7:314-317 (1991).

Maskos, et al., "A Study of Oligonucleotide Reassociation Using Large Arrays of Oligonucleotides Synthesised on a Glass Support", *Nucleic Acids Research*, 21:4663-4669 (1993).

Medlin, "The Amazing Shrinking Laboratory", *Environmental Health Perspectives*, 103:244-246 (1995).

Nguyen et al., "Differential Gene Expression in the Murine Thymus Assayed by Quantitative Hybridization of Arrayed cDNA Clones," *Genomics*, 29:207-216 (1995).

Nowak, "Entering the Postgenome Era", *Science*, 270:368-369 (1995).

Pease, et al., "Light-generated Oligonucleotide Arrays for Rapid DNA Sequence Analysis", *Proc. Natl. Acad. Sci. USA*, 91:5022-5026 (May 1994).

Pietu, et al., "Novel Gene Transcripts Preferentially Expressed in Human Muscles Revealed by Quantative Hybridization of a High Density cDNA Array", *Genome Research*, 6:492-503 (1996).

Regalado, "DNA—Chips in Genomics", *Start Up*, 1:24-30 (1996).

Sambrook, et al., "Molecular Cloning, A Laboratory Manual", *Cold Spring Harbor Press*, pp. 7.39-7.52 (1989).

Schena et al., "Structure of Homeobox-Leucine Zipper Genes Suggests a Model for the Evolution of Gene Families", *Proc. Natl. Acad. Sci. USA*, 91:8393-8397 (Aug, 1994).

Schena, "Genome Analysis with Gene Expression Microarrays", *BioEssays*, 18:427-431 (1996).

Schena, et al., "Quantitative Monitoring of Gene Expression Patterns with a Complementary DNA Microarray," *Science*, 270:467-470 (1995).

Schena, et al., "Parallel Human Genome Analysis: Microarray-based Expression Monitoring of 1000 Genes", *Proc. Natl. Acad. Sci. USA*, 93:10614-10619 (Oct. 1996).

Schena, et al., "The *HAT4* Gene of *Arabidopsis* Encodes a Developmental Regulator", *Genes & Development*, 7:367-379 (1993).

Schena, et al., "HD-Zip Proteins: Members of an *Arabidopsis* Homeodomain Protein Superfamily", *Proc. Natl. Acad. Sci. USA*, 89:3894-3898 (May 1992).

Schober, et al., "Accurate High-Speed Liquid Handling of Very Small Biological Samples", *Biotechniques*, 15(2):324-329 (1993).

Shalon, "DNA Micro Arrays: A New Tool for Genetic Analysis" (Dec. 1995) (Ph.D. Thesis, Stanford University).

Shalon, et al., "A DNA Microarray System for Analyzing Complex DNA Samples Using Two-Color Fluorescent Probe Hybridization", *Genome Research*, 6:639-645 (Jul. 1996).

Southern, et al., "Analyzing and Compaing Nucleic Acid Sequences by Hybridization to Arrays of Oligonucleotides: Evaluation Using Experimental Models", *Genomics*, 13:1008-1017 (1992).

Woolley, et al., "Ultra-high-speed DNA Fragment Separations Using Microfabricated Capillary Array Electrophoresis Chip", *Proc. Natl. Acad. Sci. USA*, 91:11348-11352 (Nov. 1994).

Zhao et al., "High-Density cDNA Filter Analysis: A Novel Approach for Large-Scale, Quantitative Analysis of Gene Expression," *Science*, 156:207-213 (1995).

Hewlett-Packard, "Peripherals Index," from *HP Fax Information Retrieval Support Technology*, Phone No. 1-800-333-1917, 6 pages.

Hewlett-Packard, "Document #9651", from *HP Fax Information Retrieval Support Technology*, Phone No. 1-800-333-1917, 3 pages.

Hewlett-Packard, "Document #5322", from *HP Fax Information Retrieval Support Technology*, Phone No. 1-800-333-1917, 5 pages.

Hewlett-Packard, "Document #5330," *HP Fax Information Retrieval Support Technology*, Phone No. 1-800-333-1917, 5 pages.

NIH grant application of P.O. Brown submitted 1992.

J.A., "Putting Genes on a Chip", *Science*, 264: (1994).

Eggers, et al.,. "A Microchip for Quantatitive Detection of Molecules Utilizing Luminescent and Radioisotope Reporter Groups," *BioTechniques*, 17:516-525 (Sep. 1994).

De Risi, et al., "Use Of a cDNA Microarray to Analyse Gene Expression Patterns in Human Cancer," *Nature Genetics*, 14:457-460 (Dec. 1996).

McGall, et al., "The Efficiency of Light-Directed Synthesis of DNA Arrays on Glass Substrates", *J. Am. Chem. Soc.*, 119:5081-5090 (1977).

Pirrung, et al., "Comparison of Methods for Photochemical Phosphoramidite-BasedDNA Synthesis," *J. Org. Chem.*, 60:6270-6276 (1995).

Southern et al., "*Molecular Interactions on Microarrays,*" Nature Genetics Supplement 21: 5-9, 1999.

Chu et al., "*Microarray-Based Immunoassays,*" Immunochemical Technology for Environmental Applications, American Cancer Society, pp. 170-187 (1997).

Meier-Ewert et al., "*An Automated Approach to Generating Expressed Sequence Catalogues,*" Nature 361: 375-376 (1993).

Nizetic et al., "*Construction, Arraying, and High-Density Screening of Large Insert Libraries of Human Chromosomes X and 21: Their Potential Use as Reference Libraries,*" Proc. Natl. Acad. Sci. USA 88: 3233-3237 (1991).

Raoult et al., "*The line Blot: an Immunoassay for Monoclonal and Other Antibodies, Its Application to the Serotyping of Gram-Negative Bacteria,*" J. Immunological Methods 125: 57-65 (1989).

Gray et al., "*Exploiting Chemical Libraries, Structure, and Genomics in the Search for Kinase Inhibitors,*" Science 281: 533-538 (1998).

Cronin et al., "*Cystic Fibrosis Mutation Detection by Hybridization to Light-Generated DNA Probe Arrays,*" Human Mutation 7: 244-255 (1996).

Saizieu et al., "*Bacterial Transcript Imaging by Hybridization of Total RNA to Oligonucleotide Arrays,*" Nature Biotechnology 16: 45-48 (1998).

Hacia et al., "*Detection of Heterozygous Mutations in BRCAI Using High Density Oligonucleotide Arrays and Two-Color Fluorescence Analysis,*" Nature Genetics 14: 441-447 (1996).

Wang et al., "*Large-Scale Identification, Mapping, and Genotyping of Single-Nucleotide Polymorphisms in the Human Genome,*" Science 280: 1077-1082 (1998).

Greenberg et al., "*Cleavage of Oligonucleotides from Solid-Phase Supports Using o-Nitrobenzyl Photochemistry,*" J. Org. Chem. 59: 746-756 (1994).

Yoo et al., "*Synthesis of Oligonucleotides Containing 3'-Alkyl Carboxylic Acids Using Universal, Photolabile Solid Phase Synthesis Supports,*" J. Org. Chem. 60: 3358-3364 (1995).

Zammattao et al., "*Comparison between Different Strategies of Covalent Attachment of DNA to Glass Surfaces to Build DNA Microarrays,*" Analytical Biochemistry 280: 143-150 (2000).

Lipshute et al., "*Using Oligonucleotide Probe Arrays to Access Genetic Diversity,*" BioTechniques 19(3): 442-447 (1995).

Lockhart et al., "*Expression Monitoring by Hybridization to High-Density Oligonucleotide Arrays,*" Nature Biotechnology 14: 1675-1680 (1996).

Schechtman, "*Isolation of Telomere DNA from Neurospora crassa,*" Molecular and Cellular Biology 7(9): 3168-3777 (1987).

Rosenbluth et al., "*Pairing for Recombination in LGV of Caenorhabditis elegans: A Model Based on Recombination in Deficiency Heterozygotes,*" Genetics 124: 615-625 (1990).

Clark et al., "*Analysis of Lethal Mutations Induced in a Mutator Strain that Activates Transposable Elements in Caenorhabditis elegans,*" Genome 33:109-114 (1990).

Pritchard et al., "*Nucleotide Sequence of the Mitochondrial Genome of Paramecium,*" Nucleic Acids Research 18(1): 173-180 (1990).

Adams et al., "*Complementary DNA Sequencing: Expressed Sequence Tags and Human Genome Project,*" Science 252: 1651-1656 (1991).

Hedgecock et al., "*The unc-5, unc-6, and unc-40 Genes Guide Circumferential Migrations of Pioneer Axons and Mesodermal Cells on the Epidermis in C. elegans,*" Neuron 2: 61-85 (1990).

Broach, "*Genes of Saccharomyces cerevisiae,*" The Molecular Biology of the Yeast Saacharomyces, Cold Spring Harbor Laboratory, pp. 653-657 (1981).

Sundberg et al., "Spatially-Addressable Immobilization of Macromolecules on Solid Supports," J. Am. Chem. Soc. 117(49): 12050-12057 (1995).

Amy Savage Blawas, "*Photopatterning of Protein Features Using Caged-Biotin-Bovine Serum Albumin,*" Ph.D. Dissertation, Department of Biomedical Engineering, Duke University (1998).

Forman et al., "*Thermodynamics of Duplex Formation and Mismatch Discrimination on Photolithographically Synthesized Oligonucleotide Arrays,*" ACS Symposium Series, Molecular Modeling of Nucleic Acids 682: 206-228 (1998).

Maskes et al., "*Oligonucleotide Hybridisations on Glass Supports: a Novel Linker for Oligonucleotide Synthesis and Hybridisation Properties of Oligonucleotides Synthesized in situ,*" Nucleic Acids Research 20(7): 1679-1684 (1992).

Marshall et al., "*DNA Chips: an Array of Possibilities,*" Nature Biotechnology 16: 27-31 (1998).

Blawas et al., "*Step-and-Repeat Photopatterning of Protein Features Using Caged-Biotin-BSA: Characterization and Resolution,*" Langmuir 14: 4243-4250 (1998).

Bannwarth et al., "*Laboratory Methods, A system for the Simultaneous Chemical Synthesis of Different DNA fragments on Solid Support,*" DNA 5(5): 413-419 (1986).

Geysen et al., "*Strategies for Epitope Analysis Using Peptide Synthesis,*" J. Immunological Methods 102: 259-274 (1987).

\* cited by examiner

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Phage

<400> SEQUENCE: 1
cctctatact ttaacgtcaa gg     22

<210> SEQ ID NO 2

-continued

```
<211> LENGTH: 20
<212> TYPE: DNA
<213> ORGANISM: Artificial Sequence
<220> FEATURE:
<223> OTHER INFORMATION: Phage

<400> SEQUENCE: 2 ttgtgtgga attgtgagcg g                                              20
```

SUBSTRATES COMPRISING POLYNUCLEOTIDE MICROARRAYS

The present invention is a continuation of U.S. patent application Ser. No. 08/688,488 for "Method For Analyzing Gene Expression Patterns", filed Jul. 30, 1996, now U.S. Pat. No. 7,323,298 which is a Continuation-in-part of U.S. patent application Ser. No. 08/514,875 for "Method and Gene-Array Device for Analyzing Gene Expression Patterns", filed Aug. 14, 1995, now U.S. Pat. No. 7,378,236 which is a continuation-in-part of U.S. patent application Ser. No. 08/477,809 for "Method and Apparatus for Fabricating Microarrays of Biological Samples", filed Jun. 7, 1995, now U.S. Pat. No. 5,807,522, which is -a continuation-in-part of U.S. patent application Ser. No. 08/261,388 for "Method and Apparatus for Fabricating Microarrays of Biological Samples", filed Jun.. 17, 1994 now abandoned. These four applications are incorporated herein by reference.

The United States government may have certain rights in the present invention pursuant to Grant No. HG00450 by the National Institutes of Health.

FIELD OF THE INVENTION

This invention relates to a method for determining the relative abundances of a plurality of polynucleotide sequences.

References

Adams, M. D., et al., *Science* 252:1651 (1991).
Adams, M. D., et al., *Nature* 355:632 (1992).
Ausubel, F. M., et al., Eds., in *CURRENT PROTOCOLS IN MOLECULAR BIOLOGY*, Greene & Wiley Interscience, New York, N.Y. (1994).
Baeuerle, P. A., et al., *Annu. Rev. Immunol.* 12:141 (1994).
Becker, J., and Craig, E. A., *Euro. J. Biochem.* 219:11 (1994).
Bohlander, et al., *Genomics* 13:1322 (1992).
Chan, A. C., et al., *Annu. Rev. Immunol.* 12:555 (1994).
Cohen, G. B., et al., *Cell* 80:237 (1995).
Collins, F. S., *Proc. Natl. Acad. Sci. USA* 92:10821 (1995).
Crabtree, G. R., et al., *Annu. Rev. Biochem.* 63:1045 (1994).
Craig, E. A., et al., *Cell* 78:365 (1994).
Cyr, D. M., *Trends Biochem. Sci.* 19:176 (1994).
Jakob, U., et al., *Trends Biochem. Sci.* 19:205 (1994).
Jindal, S., *Trends Biotechnol.* 14:17 (1996).
Lehrach, H., et al., "Hybridization Fingerprinting in Genome Mapping and Sequencing," in *GENOME ANALYSIS VOLUME 1: GENETIC AND PHYSICAL MAPPING* (Davies, K. E., and Tilgham, S. M., Eds.) Cold Spring Harbor Laboratory Press, (Cold Spring Harbor, N.Y.) pp. 39-80 (1990).
Liou H.-C., et al., *Curr. Op. Cell Biol.* 5:477 (1993).
Mullis, K. B., et al., U.S. Pat. No. 4,683,195, issued Jul. 28, 1987.
Nelson, S. F., et al., *Nature Genetics* 4:11-17 (1993).
Newton, A. C., *J. Biol. Chem.* 270:28495 (1995).
Nishizuka, Y., *FASEB J.* 9:484 (1995).
Riles, et al., *Genetics* 134:81 (1993).
Rohan, P. J., et al., *Science* 259:1763 (1993).
Sambrook, J., et al. , in *MOLECULAR CLONING: A LABORATORY MANUAL*, Second Edition, Cold Spring Harbor Laboratory (Cold Spring Harbor, N.Y.) (1989).
Schena, M., et al., *Science* 270:467-470 (1995).
Shalon, D., thesis, Stanford University (1995).
Thanos, D., et al., *Cell* 80:529 (1995).
Wilkinson, K. D., *Annu. Rev. Nutr.* 15:161 (1995).

BACKGROUND OF THE INVENTION

With a large number of human genes now identified through the Human Genome Project, there is great interest in finding out how these genes act in concert to regulate the whole organism (Watson, Collins, 1995; Adams, et al., 1991, 1992; Cohen, et al., 1995; Chan, et al., 1994; Crabtree, et al., 1994).

The current focus of this research is in monitoring the genes' activities, i.e., levels of expression, as a function of cell type, cell condition, disease state, or drug therapy response. The general requirements of this type are severalfold:

First, the method must be able to handle large numbers of genes at once. Ideally, all or nearly all expressed genes from a given cell type may be represented.

Secondly, the method should be responsive to relatively small, as well as to large, changes in the levels of expression. For example, in monitoring the response of genes in a cell exposed to a given drug, it may be important to detect slight changes in levels of expression of genes, i.e., a two-fold increase or decrease in expression level, in order to identify drug-responsive genes. As another example, in studying the response of genes in a given disease state, e.g., tumor state, it may be important, in understanding the relationship between gene expression and disease state, to classify genes according to low, moderate, and high shifts in gene expression. More generally, the greater resolution that can be achieved, in terms of relative levels of expression, the more information that can be obtained from the studies.

Finally, the method should be amenable to small amounts of polynucleotide sample material, to obviate the need for amplification of sample material, with the attendant possibility of differential amplification.

A variety of methods for studying changes in gene expression have been proposed heretofore. One approach is based on differential hybridization between nucleic acid fractions from control and test sources. After hybridization of cDNA's from the two sources, those species "equally expressed" can be removed as DNA hybrids, leaving overexpressed or underexpressed cDNA's in single-stranded form. The single-stranded species can then be further characterized, e.g., by electrophoretic fractionation.

This approach has been useful as a starting point for isolation or characterization of polynucleotides of interest in a polynucleotide mixture, but is not suited to following small changes in expression levels, or tracking changes in a relatively large number of genes.

Another approach for comparing the relative abundances of polynucleotides in mixtures involves hybridizing individual labeled probe mixtures with different replicate filters containing immobilized gene sequences, e.g., colonies of cloned DNA. Colonies on the replicate filters which hybridize differentially to the two probe mixtures then represent gene sequences which are present in greater or lesser abundance in the two probe mixtures.

Because this method relies on comparing the amounts of label at corresponding positions on two different substrates (or filters), the resolution of the method is limited by (i) variations in the amount of immobilized DNA at corresponding array positions on the two different filters, (ii) variations in the extent of hybridization that occurs at corresponding array position, e.g., due to differences in probe accessibility to the immobilized DNA, and (iii) variations in measured reporter levels at corresponding array positions. To improve the resolution appreciably, one would have to average out these variations by conducting many hybridization measurements in parallel.

It would thus be useful to provide, for measuring the relative abundances of polynucleotides in complex mixtures, an improved method that avoids or overcomes the limitations above. In particular, the method should be adaptable to measuring the relative abundances, copy numbers or expression levels in a very large number (e.g., 50,000 to 100,000) of genes, at a high resolution, e.g., two-fold change in relative abundance, and at high sensitivity for rare genes. At the same time, the method should be simple to carry out.

SUMMARY OF THE INVENTION

The present invention is directed to a method of determining the relative amounts of individual polynucleotides in a complex mixture of different-sequence polynucleotides. The method includes labeling the polynucleotides with a fluorescent reporter, and contacting the labeled polynucleotides, under hybridization conditions, with an array of different DNA sequences disposed at discrete locations on a non-porous surface, at a density of at least about 100 sequences/cm$^2$. The different DNA sequences in the array are each present in multiple copies, and are effective to hybridize to individual polynucleotides in the mixture. The level of fluorescence at each position in the microarray is then determined.

The labeled polynucleotides are preferably contacted with the microarray by covering the array surface with a solution of the mixture of labeled polynucleotides, to a solution depth of less than 500 microns.

In various preferred embodiments, the density of array elements corresponding to different-sequence DNA locations in the array is at least 1,000/cm$^2$, the DNA sequences in the array are at least about 50 bases in length, and the labeled polynucleotides represent at least 1 million unique base sequences.

The method may be used in determining the relative amounts of each polynucleotide from first and second different sources. Here (i) the polynucleotides from the first and second sources are labeled with independently detectable first and second fluorescent reporters, respectively, (ii) the contacting of labeled polynucleotides from first and second sources is carried out simultaneously under competitive hybridization conditions, and (iii) the determining step includes measuring the levels of the two reporters at each position in the array.

These and other objects and features of the invention will become more fully apparent when the following detailed description of the invention is read in conjunction with the accompanying figures.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

DETAILED DESCRIPTION OF THE INVENTION

I. Definitions

Figure 1:
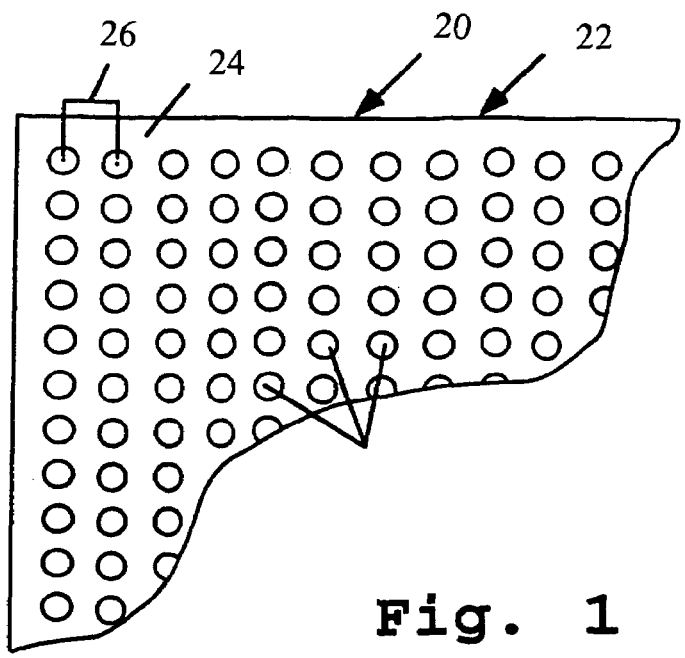
FIG. 1 shows a portion of a two-dimensional microarray of different DNA sequences used in practicing the method of the invention.

Unless indicated otherwise, the terms defined below have the following meanings:

A "polynucleotide" refers to a DNA or RNA polymer at least about 50 bases in length, i.e., containing at least about 50 nucleotide subunits.

"Different-sequence polynucleotides" refers to polynucleotides having different, unique base sequences. Such polynucleotides are distinguished by their ability to hybridize selectively to complementary-strand nucleic acid sequences under selected hybridization conditions.

A "complex mixture of different-sequence polynucleotides" refers to a mixture containing a plurality, and preferably at least 100, different-sequence polynucleotides. The complexity of the mixture is defined by the aggregate unique base sequence in the different-sequence polynucleotides. For example, a mixture of 1,000 polynucleotides, each containing 1,000 unique base sequences, will have a complexity of 1 million bases.

A "microarray of DNA sequences" refers to a spatial array of nucleic acid polymers, e.g., polymers of at least 15-20 bases, preferably polynucleotides of 50 bases or more, having a different DNA sequence at the different microarray locations. The different sequences may be of known sequence, or partially or completely sequenced, as with polymers prepared by solid-phase synthesis, primer-amplified genomic DNA fragments or expressed-sequence tags (EST clones) (Adams, et al., 1991, 1992), or they may be unsequenced, as with library cDNA's isolated from a library. The array may also contain regions with different graded concentrations or sequence lengths of same-sequence polynucleotides, and/or mixtures of two or more different sequences. The different DNA sequences may also include DNA analogs, such as analogs having phosphonate or phosphoramidate backbones, capable of hybridizing, through Watson-Crick base pairing, with complementary-sequence DNA or RNA. The microarray has a density of distinct gene sequences of at least about $100/cm^2$, for example about $400/cm^2$, and preferably at least about $1,000/cm^2$. The regions in a microarray have typical dimensions, e.g., diameters, in the range between about 10-500 μm, for example about 250 μm, and are separated from other regions in the same array by about the same distance.

The support is a polymer, glass, or other solid-material support having a preferably planar, hydrophobic surface. The hydrophobic surface may be formed by the support material, or by a coating applied to the support. The important "hydrophobic" property of the support surface is that it produces beading of aqueous reagent solution applied to the surface. A variety of known hydrophobic polymers, such as polystyrene, polypropylene, or polyethylene have desired hydrophobic properties, as do glass and a variety of lubricant or other hydrophobic films that may be applied to the support surface.

"Cells of a given cell type or types" refers to cells obtained from one or more particular tissues or organs, e.g., hepatocytes, heart muscle cells, pancreatic cells, or non-differentiated embryonic tissue, or to a particular blood cell type or types, e.g., peripheral blood lymphocytes.

Cells having a "selected physiological state or disease condition" or "test cells" refer to cells of a given cell type or types which, as examples, (i) are in a defined state of differentiation or activation, e.g., by gene activation; (ii) are infected by a defined infectious agent, e.g., HIV-infected T cells; (iii) are in a neoplastic state, i.e., tumor cells; (iv) are in a chemical- or physical-response state, i.e., after exposure to a pharmacological agent with respect to control cells of the same type or types; (v) are in a defined stage of cell cycle; (vi) have a particular chronological age; (vii) are undergoing response to an extracellular signal; (viii) have a genetic defect; (ix) are from a patient with a particular physiological disease state; or (x) are taken from particular anatomical locations or microenvironments.

Cells which are in a normal or control or an alternative reference state with respect to "test cells" are referred to herein as "control cells". "Reporter-labeled copies of messenger nucleic acid" refers to reporter-labeled mRNA transcripts obtained from test or control cells or cDNAs produced from such transcripts. The reporter label is any detectable reporter, and typically a fluorescent reporter.

A "cDNA" refers to a cloned, amplified, synthesized, single-stranded, double-stranded, or first strand product DNA corresponding in sequence to all or a portion of an mRNA.

II. DNA Sequence Microarrays

This section describes microarrays of different DNA sequences disposed at discrete locations on a non-porous surface, at a density of at least about 100 sequences/$cm^2$. The DNA sequences in the array are each (i) present in multiple copies, and (ii) effective to hybridize to an individual polynucleotide in a mixture of polynucleotides, in accordance with the method of the invention.

Methods of forming microarrays of this type have been detailed in the above-cited, co-owned U.S. patent application Ser. Nos. 08/514,875, 08/477,809, and 08/261,388, and related PCT application WO/95/35505, published Dec. 28, 1995, all of which are incorporated by reference herein. Details are also given in the Methods below.

Briefly, a capillary- or tweezer-like fluid dispenser in a robotic apparatus is employed to pick up a selected DNA solution from a solution source, and distribute the solution to each of a plurality of non-porous microarray substrates, at a selected microarray location on the substrate surface, and in a selected amount (solution volume). A droplet of solution is deposited on the substrate surface by tapping the dispenser on the substrate at the selected deposition region. The volume of material deposited can be controlled according to the dimensions of the dispenser, the tapping force, the viscosity of solution, and the duration of application, to achieve a selected deposition volume, as described in the above co-owned patent applications. Typically deposition volumes are between about $2 \times 10^{-3}$ to 2 nanoliters (nl), corresponding in droplet size (surface diameter) between about 20 to 200 μm. The DNA in the each microarray region is preferably present in a defined amount between about 0.1 femtomoles and 100 nanomoles.

This operation is repeated for each microarray position, until the array is completed, with a different DNA sequence at each position (recognizing that some microarray positions may be duplicates with the same or different amounts of a single sequence, and some microarray positions may contain combinations of two or more different DNA sequences).

As noted above in the definitions above, the regions of the microarray are about 20-500 μm in diameter, preferably about 50-200 μm, with spacing between adjacent regions on the microarray surface of about the same dimensions. The microarray density is at least 100/$cm^2$, and preferably at least 1,000/$cm^2$. Thus, for example, an array having 100 μm size DNA spots, each separated by 100 μm, will have a density of about 2,500 regions/$cm^2$.

The non-porous substrate surface on which the different DNA sequences are deposited may be any surface capable of supporting an aqueous layer on the surface without liquid absorption or flow into or through the substrate; that is, any substrate surface which is water-impermeable. Preferred substrates are glass slides, metalized surfaces, non-porous polymer substrates, such as polyethylene, polyurethane, or polystyrene sheet material, or substrates which are coated with a non-permeable film or layer.

In the case where the DNA sequences are to be covalently attached to the substrate surface, the substrate includes or is treated to include chemical groups, such as silylated glass, hydroxyl, carboxyl, amine, aldehyde, or sulfhydryl groups. After deposition of the DNA sequences on the substrate surface, and either before or after drying the solution at each array location, the DNA is fixed by covalent attachment to the surface. This may be done, for example, by drying the DNA spots on the array surface, and exposing the surface to a solution of a cross-linking agent, such as glutaraldehyde, boro-hydride, or any of a number of available bifunctional agents. one such linking method is detailed in the Methods section below.

Alternatively, the DNA sequences may be attached to the substrate surface non-covalently, and typically by electrostatic interaction between positively charged surface groups and the negatively charged DNA molecules. In one preferred embodiment, the substrate is a glass slide having formed on its surface, a coating of a polycationic polymer, preferably a cationic polypeptide, such as polylysine or polyarginine, as described in the Methods section below. In experiments conducted in support of the invention, as illustrated in Example 1 and 2, it has been discovered that the non-covalently bound polynucleotides remain bound to the coated slide surface when an aqueous DNA sample is applied to the substrate under conditions which allow hybridization of reporter-labeled polynucleotides in the sample to complementary-sequence (single-stranded) polynucleotides in the substrate array.

The DNA sequences forming the microarray are polynucleotides having lengths of about 50 bases or greater, although shorter DNA polymers, e.g., in the range 15-50 bases may also be employed. These DNA sequences can be formed by a variety of methods, including solid-phase synthesis, polymerase chain reaction (PCR) methods, gene cloning, gene cloning in combination with PCR, and solid-phase methods. The DNA sequences on the array have the same sequence as some, and preferably a large number, of the polynucleotides in the complex mixture which will be reacted with the microarray. That is, the microarray sequences will hybridize with selected polynucleotides in the polynucleotide mixture. Moreover, the hybridization is selective, meaning that one array sequence will typically hybridize with one species only in the polynucleotide mixture. This requirement would exclude relatively short, e.g., less than 8-10 base oligonucleotides as array DNA sequences and/or combinatorial oligonucleotides such as are used for sequencing by hybridization.

Preferred sources of DNA sequences in the microarrays are genomic sequences and mRNA-derived sequences, as illustrated in the examples below. DNA sequences from genomic sources are typically obtained from cloned genomic fragments corresponding predominantly to single-copy or low-copy number genes, i.e., excluding repeat-sequence genomic fragments, or by primer-amplification of transcribed regions of a genome.

The cloned fragments may be excised and/or PCR-amplified, then purified by conventional methods, such as described in the Methods below. Alternatively the fragments may be obtained directly from genomic sources, e.g., from genomic fragments that have been treated to remove repeat sequences, and/or by PCR amplification methods. For example, using computer-aided sequence analysis, it is possible to construct PCR primers for expressed genomic sequences, to selectively generate these sequences. The purified genomic sequences applied to the microarray surface may be partially or completely sequenced, or may have unknown sequences.

DNA sequences derived from mRNA's can include mRNA's themselves, but more commonly sequences produced by reverse transcription of mRNA's, or DNA sequences obtained from a library of cloned cDNA's, e.g., by excision or primer amplification. The mRNA's are preferably obtained from cells having a selected physiological state or disease condition and from corresponding test cells, as defined above, according to known methods. The mRNA-derived sequences applied to the microarray surface may be completely sequenced, partially sequenced, e.g., as for expressed sequence tags (EST's), or may have unknown sequences.

Figure 2:
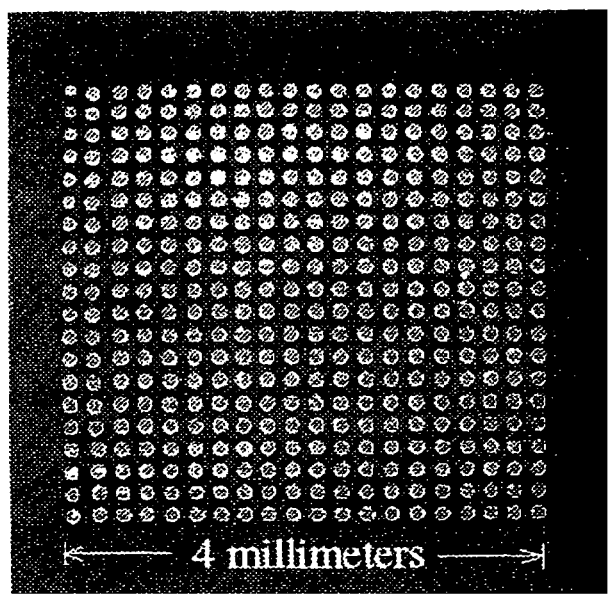
FIG. 2 shows a fluorescent image of an actual 20×20 array of 400 fluorescently-labeled DNA samples immobilized on a poly-l-lysine coated slide, where the total area covered by the 400 element array is 16 square millimeters.

FIG. 1 shows a portion of a microarray 20 having a substrate 22 whose surface 24 contains an array of regions, such as at 26, containing different-sequence DNA's. A 20×20 array in a (4 mm)$^2$ area, and thus having a density of about 2,500 regions/cm$^2$ is shown in FIG. 2. The array is formed as described in Example 1.

III. Microarray Method

The method of the invention is designed to measure the relative abundances of polynucleotides in a complex mixture of polynucleotides. As defined above, a complex mixture preferably contains at least about 50, and up to 1,000 or more polynucleotides with different sequences. The complexity of the mixture is defined by the number of unique polynucleotide sequences and is preferably at least 10$^6$, e.g., containing 1000 different-sequence polynucleotides having an average of at least 1,000 bases.

Genomic fragments of the type described in Section II above represent one source of polynucleotides, where the method is used to determine the relative abundance of different genomic species, e.g., from a selected chromosome or region of a chromosome, or chromosomes of a given cell type. Methods of obtaining genomic fragments suitable for the method are described above, or are known, e.g., as described in U.S. Pat. No. 5,376,526.

Polynucleotides derived from mRNA's as above represent another source of polynucleotides, where the method is used to determine the relative abundance of mRNA's from a given cell source, for purposes of measuring the relative levels of gene expression of a plurality of genes, e.g., from the cell source. Methods for obtaining mRNA-derived polynucleotides, e.g., corresponding to all of the expressed genes in a given cell type, are well known.

In practicing the method of the invention, the polynucleotides in the mixture are labeled with a fluorescent reporter. The fluorescent labeling can be carried out by standard methods, typically by transcribing DNA in the presence of fluorescence labeled nucleotides, such as Cy5-dNTP or fluorescent-labeled dNTP. Labeling may be carried out in vitro or in vivo.

In one embodiment of the invention, described below, mixtures of polynucleotides from two different cell sources, referred to herein as test and control cells, are labeled with different fluorescent reporters which have independently detectable fluorescent properties, typically different fluorescent-emission peaks. The two independently labeled mixtures are then combined.

The mixture of labeled polynucleotides is contacted with the microarray surface, under conditions which permit hybridization between microarray sequences and complementary sequences in the mixture. The amount of polynucleotide mixture added to the microarray should be less than that which would saturate most of the array regions. In a preferred embodiment, a mixture of polynucleotides having a solution concentration of between about 0.1 to 10 μg DNA/μl is placed on the microarray surface, in a total volume of between about 0.5-10 μl/cm² microarray surface, and the surface is covered with a glass coverslip. In this configuration, the "thickness" of the polynucleotide mixture is preferably between 10 and 500 μm.

When the polynucleotide mixture is double-stranded DNA, the double-stranded species may be denatured before application to the microarray surface, e.g., by heating above the denaturation temperature, then rapidly cooling, as described in Example 1 below. Alternatively, the double-stranded material may be denatured by heating after addition to the slide, then cooled to permit hybridization.

Standard hybridization conditions for hybridizing labeled polynucleotides to the complementary-sequence DNA sequences on the microarray are employed, preferably to an end point at which complete hybridization is achieved, as detailed in the Methods below. The salt and temperature conditions of hybridization are selected for a desired stringency, according to well known principles, and/or the array is washed after hybridization at high stringency salt and temperature conditions.

After hybridization, the microarrays are washed, then scanned for fluorescence intensity. The scanning may be carried out with a confocal laser scanning device, as detailed in the Methods below. From the scanned fluorescence data, an image of the microarray can be reconstructed, typically employing software to convert image intensity, which may vary over 3-4 logs, to a color or gray-scale intensity.

Where the array being scanned contains two fluorescent labels, each label is scanned independently at a selected excitation wavelength. After correcting for optical crosstalk between the fluorophores, due to their overlapping emission spectra, the combined pattern may be represented as two separate images, in which the intensity of each label at each array position is represented, for example, in terms or a color or gray scale. FIGS. 4A and 4B, and 5A and 5B, discussed below, are illustrative.

Figure 6:
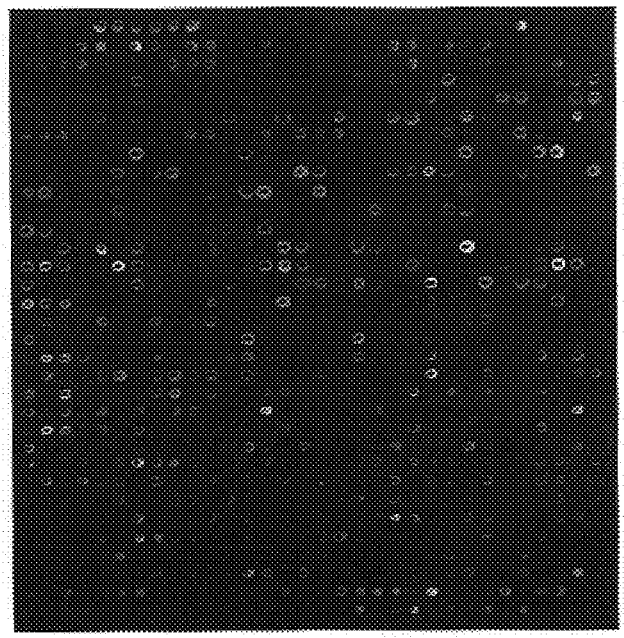
FIG. 6 shows a combined two-color scan of a microarray containing 1,046 cDNA's from peripheral blood lymphocytes (PBL's) after hybridization with a mixture of cDNA's from bone marrow labeled with Cy5-dCTP and cDNA's from Jurkat cells labeled with fluorescein-dCTP, where red spots indicate greater gene expression levels in bone marrow, green spots, greater gene expression levels in Jurkat cells, and yellow spots, comparable gene expression levels in both cells.
Figure 7:
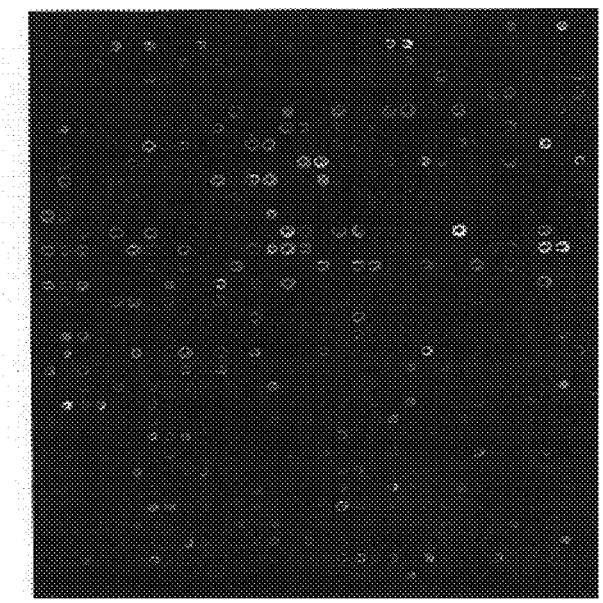
FIG. 7 shows a combined two-color scan of a microarray containing 1,046 cDNA's from peripheral blood lymphocytes (PBL's) after hybridization with a mixture of cDNA's from heat-shocked Jurkat cells labeled with Cy5-dCTP and cDNA's from control Jurkat cells labeled with fluorescein-dCTP, where red spots indicate greater gene expression levels in heat-shocked cells, green spots, greater gene expression levels in unshocked cells, and yellow spots, comparable expression gene expression levels in both cells.
Figure 8:
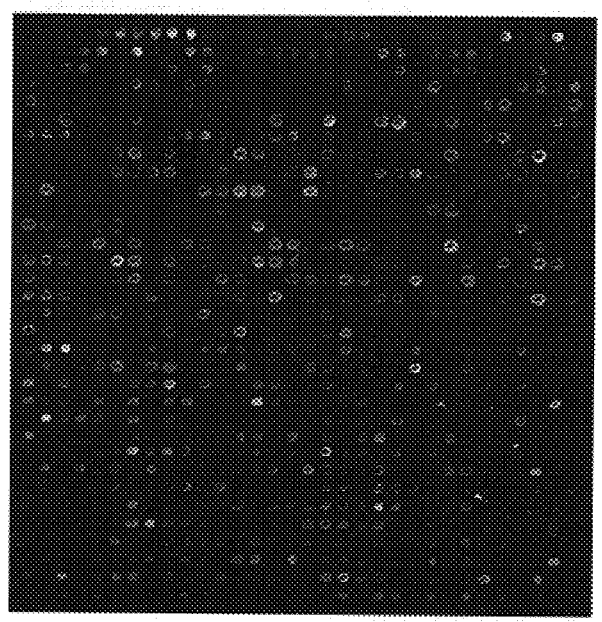
FIG. 8 shows a combined two-color scan of a microarray containing 1,046 cDNA's from peripheral blood lymphocytes (PBL's) after hybridization with a mixture of cDNA's from phorbol-ester-treated Jurkat cells labeled with Cy5-dCTP and cDNA's from control Jurkat cells labeled with fluorescein-dCTP, where red spots indicate greater gene expression levels in phorbol-ester treated cells, green spots, greater gene expression levels in untreated cells, and yellow spots, comparable expression gene expression levels in both cells.
Figure 11:
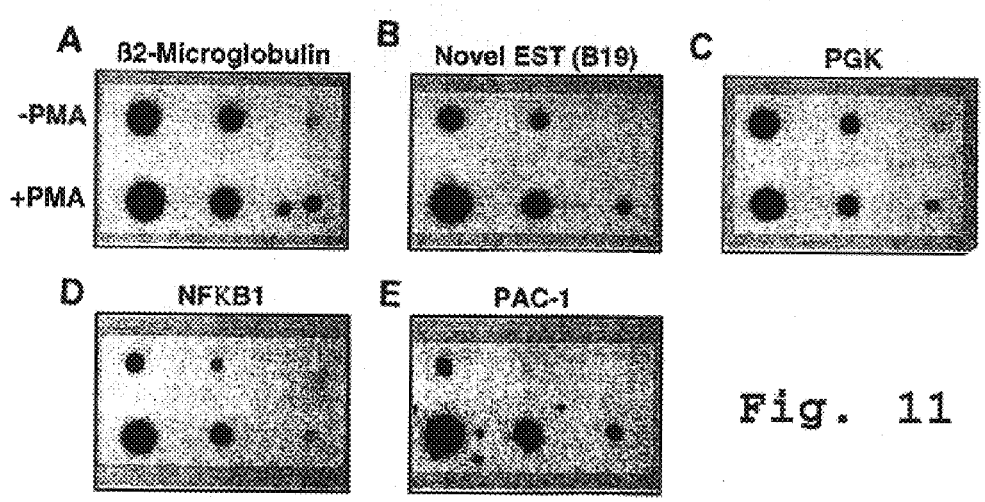
FIGS. 11A-11E are Northern RNA "dot" blots of samples of RNAs from control Jurkat cells (−PMA) or phorbol-ester-treated Jurkat cells (+PMA), after spotting onto nylon membranes, and blotting with the designated cDNA probes from Table 1.

Alternatively, in the case of a two-color image, each label may be represented with a different color, e.g., red and green, at a color intensity corresponding to the measured intensity of that fluorophore. This representation has the advantage of allowing quick visual assessment of microarray regions where one or the other fluorophore dominates in polynucleotide abundance (as evidenced, for example, by predominantly red or green spots), or where equal abundances of the two species are present (as evidenced, for example, by yellow spots). This type of representation is seen in FIGS. 6-8, discussed below.

As discussed below, the method allows for detection of changes in relative abundance between different polynucleotides on the array, and between the same polynucleotide from two different sources, of 20-50% or less. Thus, where the method is used to determine relative levels of gene expression in a plurality of genes from two different cell sources, very small changes in expression, e.g., 20%, can be detected. As will be illustrated below, this sensitivity allows large numbers of genes, e.g., all genes whose mRNA is present at a level or at least $1:10^6$ and $1:10^7$, to be simultaneously monitored for both major and slight variations in gene expression, in response to a given change in cell state or cell type. This capability, in turn, allows for the simple identification of many new genes that are up-regulated or down-regulated in response to a particular shift in cell state or type.

IV. Applications

The method described above has a variety of applications, including genetic and physical mapping of genomes, genetic diagnosis, genotyping of organisms, monitoring of gene expression, and gene discovery.

A. Genetic Analysis

For genetic analysis, a plurality of polynucleotides, e.g., cloned genomic fragments, is hybridized to an ordered array of DNA fragments—typically cloned genomic fragments—and the identity of the DNA elements applied to the array is unambiguously established by the pixel or pattern of pixels of the array that are detected.

One application of such arrays for creating a genetic map is described by Nelson, et al. (1993). In constructing physical maps of the genome, arrays of immobilized cloned DNA fragments are hybridized with other cloned DNA fragments to establish whether the cloned fragments in the probe mixture overlap and are therefore contiguous to the immobilized clones on the array. For example, Lehrach, et al. (1990), describe such a process.

Figure 3A:
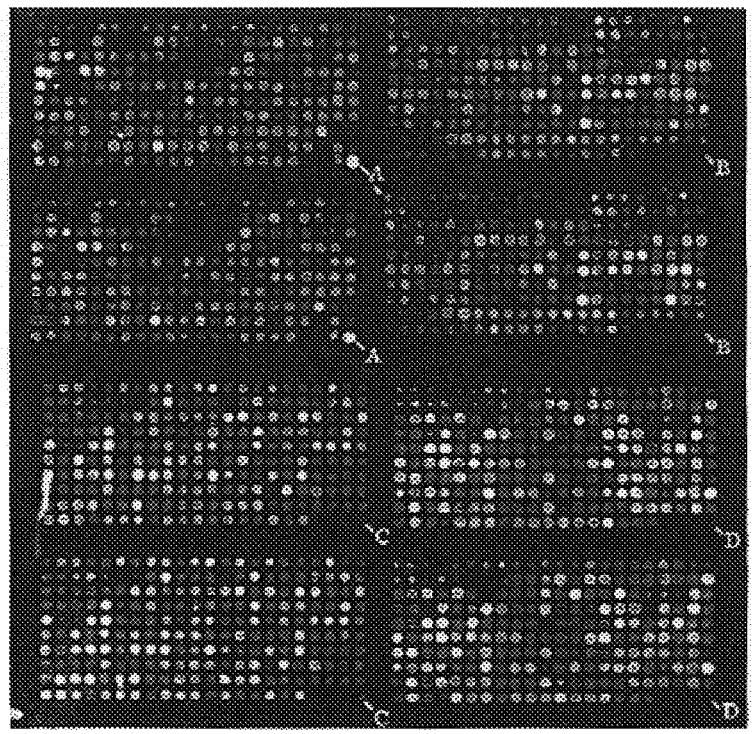
FIG. 3A is a fluorescent image of a 1.8 cm×1.8 cm microarray containing lambda clones with yeast inserts, the fluorescent signal arising from the hybridization to the array with approximately half the yeast genome labeled with a green fluorophore and the other half with a red fluorophore.

Example 1 illustrates an application of the method, for studying genomic complexity in *S. cerevisiae*. Here genomic fragments from the six largest yeast chromosomes were labeled with one fluorescent tag, and fragments from the 10 smallest chromosomes, with another tag, and the two labeled fragment mixtures were hybridized with a microarray of DNA sequences representing cloned yeast genomic fragments. The results are shown in FIG. 3A. A red signal in the figure indicates that the lambda clone on the array surface contains a cloned genomic DNA segment from one of the largest six yeast chromosomes. A green signal indicates that the lambda clone insert comes from one of the smallest ten yeast chromosomes. Orange signals indicate repetitive sequences which cross hybridized to both chromosome pools. Control spots on the array confirm that the hybridization is specific and reproducible.

Figure 3B:
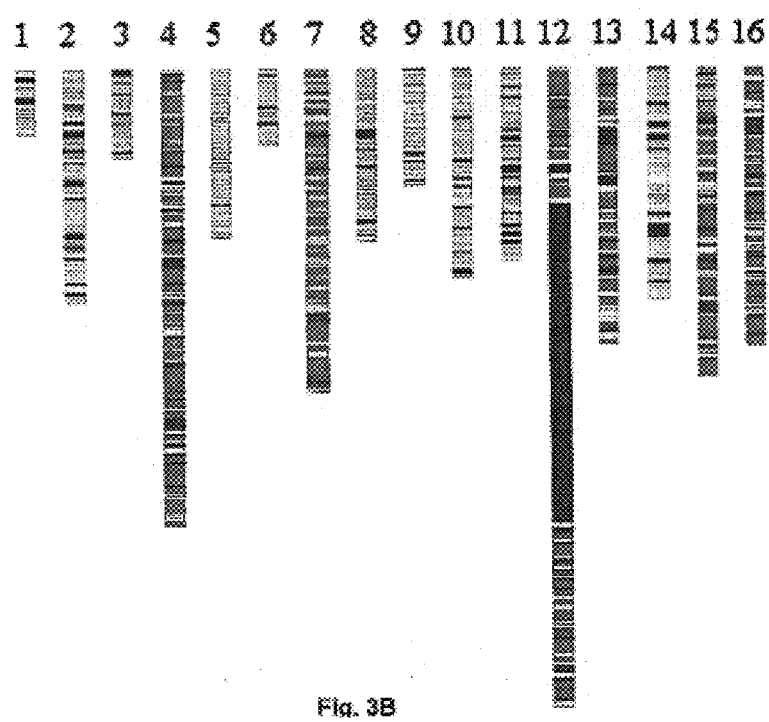
FIG. 3B shows the translation of the hybridization image of FIG. 3A into a karyotype of the yeast genome, based on the hybridization pattern of the FIG. 3A microarray which contains yeast DNA sequences that have been previously physically mapped in the yeast genome.

The physical map locations of the genomic DNA fragments contained in each of the clones used as array elements have been previously determined by Olson and co-workers (Riles, et al., 1993), allowing for the automatic generation of the color karyotype shown in FIG. 3B.

The color of a chromosomal section on the karyotype corresponds to the color of the array element containing the clone from that section. The black regions of the karyotype represent false negative dark spots on the array (10%) or regions of the genome not covered by the Olson clone library (90%). The largest six chromosomes are mainly red while the smallest ten chromosomes are mainly green, matching the original CHEF gel isolation of the hybridization probe. Areas of the red chromosomes containing green spots and vice-versa are probably due to spurious sample tracking errors in the formation of the original library and in the amplification and spotting procedures.

It can be appreciated how this approach can be applied to other types of genetic analysis, for example, in comparative genomic hybridization, or for use determining the extent of genetic divergence between two different species.

In all of these applications, the microarray method allows a large number of genomic sequences, e.g., $10^4$-$10^5$ or more, to be examined on a single array, using only a small amount of genetic material, and with the capability of detecting changes or differences in the relative abundance between labeled polynucleotides on the array of as little as 20%.

B. Gene Expression Analysis

In another general application, a microarray of cDNA clones representing genes from a given source, or the expressed genomic sequences from that source, is hybridized with labeled cDNA's to monitor gene expression for research or diagnostic purposes. In a one-color mode, the method is used to examine relative expression levels among the various genes represented on the microarray. Alternatively, to monitor relative levels of gene expression between the individual genes from test and control cells, each labeled cDNA mixture can be hybridized with an individual microarray, and the patterns of fluorescence intensities in the two microarrays compared.

Relative levels of gene expression from two sources can be more advantageously studied, in accordance with the method, in single-array mode where the cDNA mixtures from two different cell sources are labeled with different fluorescent labels, and hybridized simultaneously with a single microarray. The ratio of the two fluorescent labels at each array position is a measure of the differential expression of that gene in the two cell sources. The ratio measurement is independent of the absolute abundance level of that gene.

It is also possible to use more than two fluorescent tags, when examining more than two cell sources simultaneously. This approach greatly enhances the resolution of the method, i.e., the ability to detect small changes in expression level, by effectively eliminating variations between two separate microarrays in fluorescent signals due to, for example, different amounts of target sequences on the arrays.

Figure 4A:
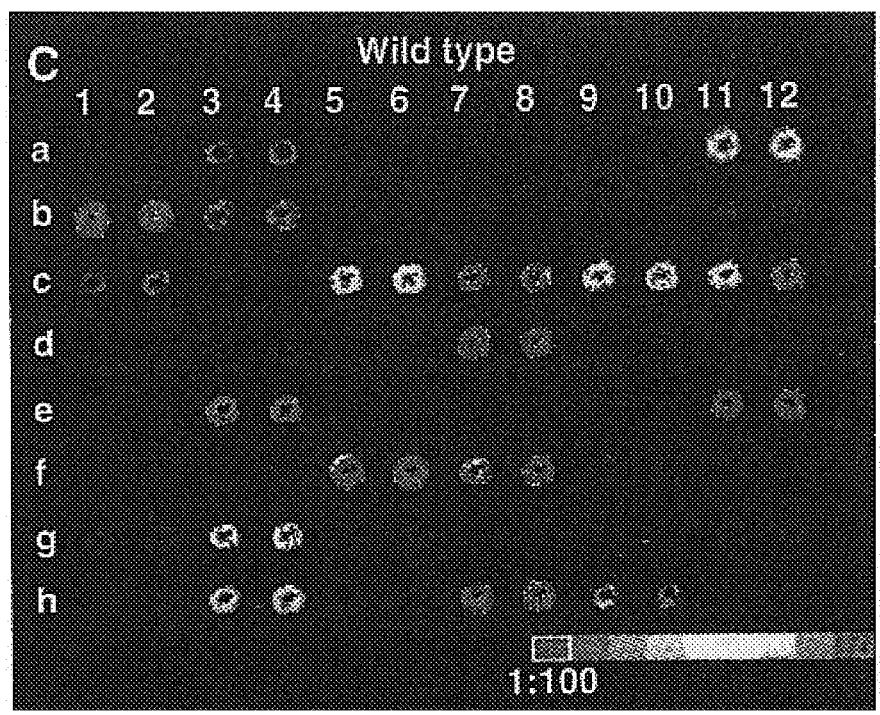
FIGS. 4A and 4B show scans of hybridization signals from an array of genes probed with fluorescently-labeled Arabidopsis wild-type (4A) or transgenic HAT4 (4B) cDNA at low photomultiplier tube settings.
Figure 4B:
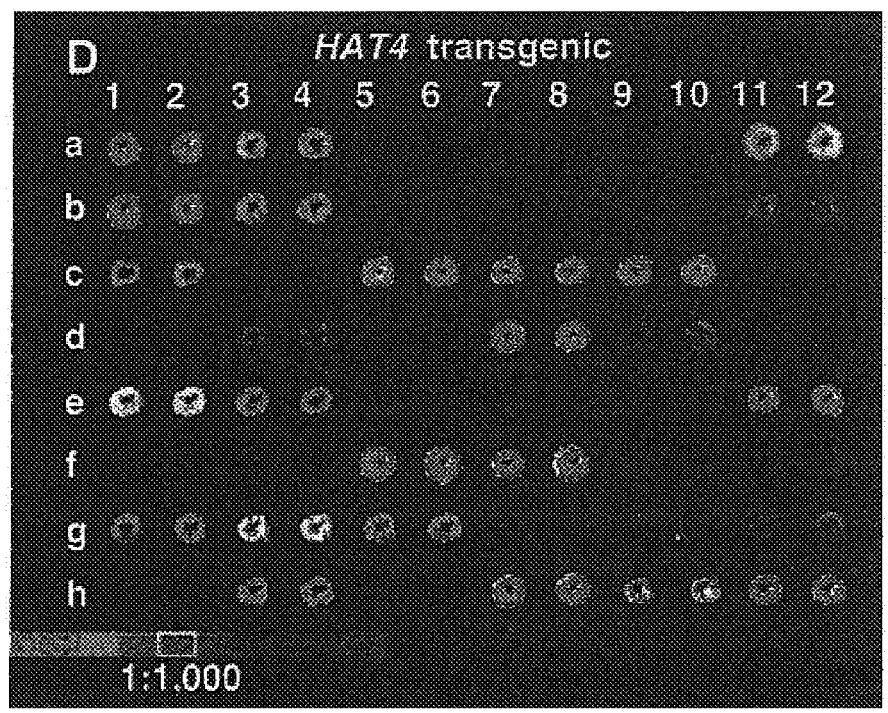

The use of the two-color method for examining gene expression levels in plants in illustrated in Example 2. Briefly, mRNA obtained from wild type and transgenic *Arabidopsis* plants containing an exogenous HAT-4 gene were isolated, and cDNA from the two sources was prepared and labeled with different fluorescent labels. The cDNA mixture was hybridized to a single microarray containing an array of *Arabidopsis* cloned cDNA's. FIGS. 4A and 4B show the fluorescent-intensity scans of the microarray for the wild type cDNA fluorescence label (4A) and the transgenic cDNA fluorescence label (4B) (both from the same microarray). The gene expression patterns differ in several respects, but in particular, by the presence in two strong spots in FIG. 4B (indicated at 49.50) corresponding to HAT-4 cDNA.

Figure 5A:
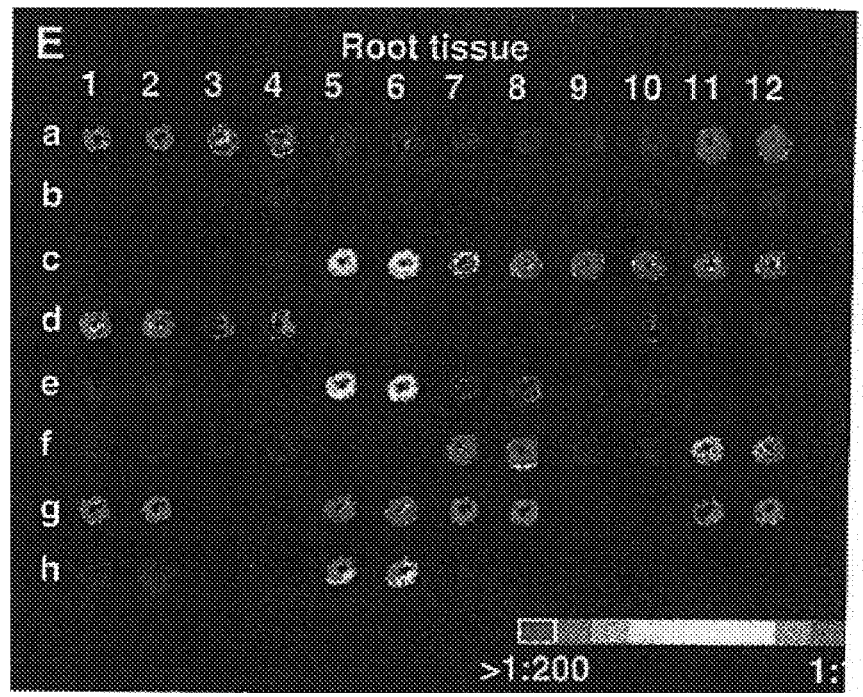
FIGS. 5A and 5B show scans of hybridization signals from an array of genes probed with fluorescently-labeled Arabidopsis wild-type root (5A) or wild-type leaf (5B) cDNA at intermediate photomultiplier tube settings.
Figure 5B:
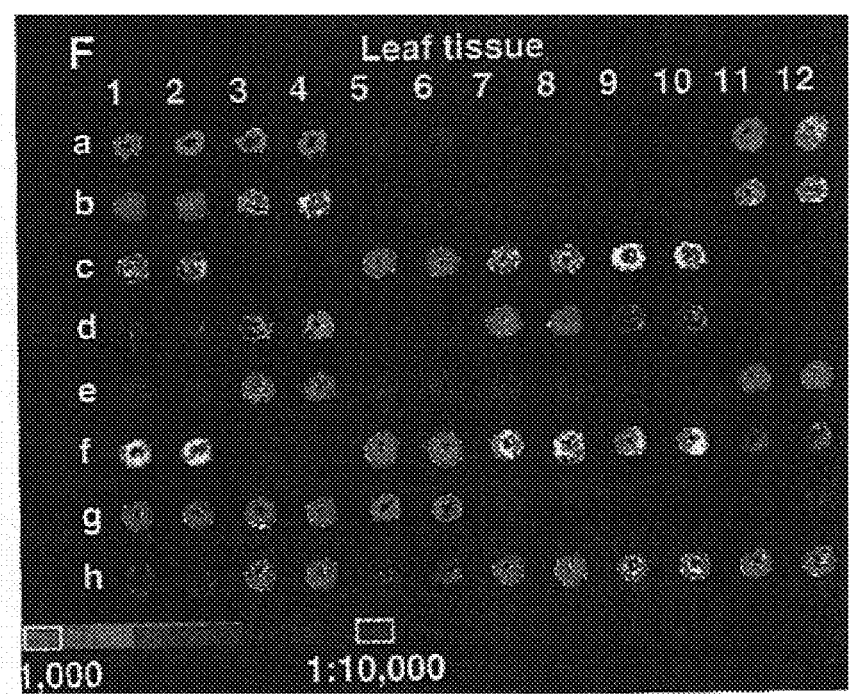

Using an identical same microarray, a similar study was carried out to examine differences in the gene expression patterns from root and leaf tissue from *Arabidopsis*, shown in FIGS. 5A and 5B, respectively. As seen, the two tissues give quite different patterns of expression for the particular cDNA sequences on the array. Details are given in Example 2.

One of the important applications of the method is the ability to identify genes that are associated with a given cell state or type. The objective of such studies is to identify new genes that can be used as diagnostic indicators of the cell state or type, and to identify new cellular enzymes and pathways, related to expression of the newly discovered genes, that can serve as targets in developing new therapeutic agents.

Heretofore, detecting levels of differential gene expression between control and test cells has been limited by the number of genes that can be examined on a single array, and the sensitivity of array methods to changes in the levels of hybridized probe. In general, these limitations significantly increase the work required to identify low-copy-number genes of interest, and may even prevent such genes from being identified.

To illustrate the method as applied to identifying new genes in human bone-stem cells, a microarray of human cDNA clones, picked at random from a human peripheral blood lymphocyte cDNA library, was prepared as detailed in Example 3. The array contained 1,046 PBL clones, and 10 sequences from *Arabidopsis*, as control sequences.

In a first study, a mixture of cDNA's from bone marrow labeled with Cy5-dCTP and cDNA's from Jurkat cells labeled with fluorescein-dCTP were hybridized to the microarray, to assess the different patterns of gene expression in the two blood-cell types. The scanned array is shown in FIG. 6, where red spots indicate higher gene expression in bone marrow, green spots, greater gene expression levels in Jurkat cells, and yellow spots, comparable gene expression levels in both cells. It is apparent from the figure that the two cell types have quite different levels of gene expression in many genes.

A second study was designed to identify genes responsive to heat shock in the Jurkat cell line. A number of heat-shock proteins in Jurkat and other cell lines have been identified, as discussed below. It was therefore of interest to see if the present method could extend the number of genes known to be responsive.

In the study, Jurkat cells, after initial culturing, were grown for 4 hours at 37° C. and 43° C., respectively. Total mRNA from the harvested control and heat-shocked cells was labeled by reverse transcriptase incorporation of fluorescein- or Cy5-derivatized dCTP, respectively, as detailed in Example 3. The two cDNA fractions were mixed and hybridized to the human PBL microarray above. The combined fluorescent scans for the two fluorophores are shown in FIG. 7.

Examination of the fluorescent scans revealed positive hybridization signals to >95% of the human cDNA array elements, but not to any of the *Arabidopsis* controls. Hybridization intensities spanned more than three orders of magnitude for the 1,046 array elements surveyed. Comparative expression analysis of heat shocked versus control cells in the two experiments revealed altered fluorescence intensities at 17 array elements. Of the 17 putative differentially expressed genes, 11 were induced by heat shock treatment and 6 displayed modest repression. This result is indicated schematically in FIG. 9A which shows up-regulated and down-regulated genes as red and green spots, respectively.

To determine the identity of the genes that exhibited altered expression patterns, cDNAs corresponding to each of the 17 array elements were subjected to single pass DNA sequencing on the proximal end of each clone (see Example 3 for details). Database searches of the sequences revealed "hits" for 14 of the 17 clones (Table 1, B1-B17); the three remaining clones (B8-B10) did not match any sequence in the public human database, though one of the clones (B7) exhibited significant homology to an expressed sequence tag (EST) from *C. elegans*. To further confirm the identity of the clones, the nucleotide sequence of the distal end of each cDNA was determined. In all cases, proximal and distal cDNA sequences mapped to the same gene.

TABLE 1

| Clone | Row | Column | Ratio | Blast Identity | Accession # |
| --- | --- | --- | --- | --- | --- |
| B1 | 2421 | | 0.5 | — | CYC oxidase III | J01415, J01415 |
| B2 | 1 | 31 | 0.5 | β-Actin | N.R., X00351 |
| B3 | 15 | 8 | 0.5 | CYC oxidase III | J01415, J01415 |
| B4 | 32 | 19 | 0.5 | CYC oxidase III | J01415, J01415 |
| B5 | 17 | 8 | 0.5 | CYC oxidase III | J01415, J01415 |
| B6 | 22 | 31 | 0.5 | β-Actin | X.R., X00351 |
| B7 | 5 | 4 | 2.0 | Novel* | U56653, U56654 |

TABLE 1-continued

| Clone | Row | Column | Ratio | Blast Identity | Accession # |
|---|---|---|---|---|---|
| B8 | 2 | 19 | 2.0 | Novel* | U56655, U56656 |
| B9 | 14 | 5 | 2.2 | Novel* | U56657, U56658 |
| B10 | 7 | 8 | 2.4 | Polyubiquitin | X04803, X04803 |
| B11 | 12 | 2 | 2.4 | TCP-1 | X52882, X52882 |
| B12 | 28 | 2 | 2.5 | Polyubiquitin | M17597, M17597 |
| B13 | 14 | 7 | 2.5 | Polyubiquitin | X04803, X04803 |
| B14 | 20 | 9 | 2.6 | HSP90° | M16660, M16660 |
| B15 | 30 | 12 | 4.0 | DnaJ homolog | D13388, D13388 |
| B16 | 10 | 5 | 5.8 | HSP90a | X07270, X07270 |
| B17 | 13 | 16 | 6.3 | HSP90a | M27024, X15183 |
| B18 | 7 | 19 | 2.0 | °-2-microglobulin | S54761, M30683 |
| B19 | 21 | 30 | 2.1 | Novel* | U56659, U56660 |
| B20 | 3 | 26 | 2.2 | °-2-microglobulin | S54761, M30683 |
| B21 | 1 | 18 | 2.6 | PPG kinase | M11968, L00160 |
| B22 | 22 | 30 | 3.5 | NF-kB1 | Z47744, M55643 |
| B23 | 20 | 16 | 19 | PAC-1 | L11329, L11329 |

The five most highly induced genes in heat-treated cells included heat shock protein 90a (HSP90α), DnaJ, HSP90β, polyubiquitin, and t-complex polypeptide-1 (TCP-1) (Table 1). HSPα, DnaJ, and HSP90 β exhibited a 6.3-, 4.0-, and 2.6-fold induction, respectively; lesser activation was observed for genes encoding polyubiquitin and TCP-1 (Table 1). Three novel sequences (B7-B9) each exhibited induction in the 2-fold range (Table 1). A modest repression was observed for both β-actin and cytochrome c (cyc) oxidase III (Table 1). In several cases, clones corresponding to the same gene were recovered at multiple locations on the array; expression ratios for these clones varied by less than 10% from element to element (Table 1).

Figure 10:
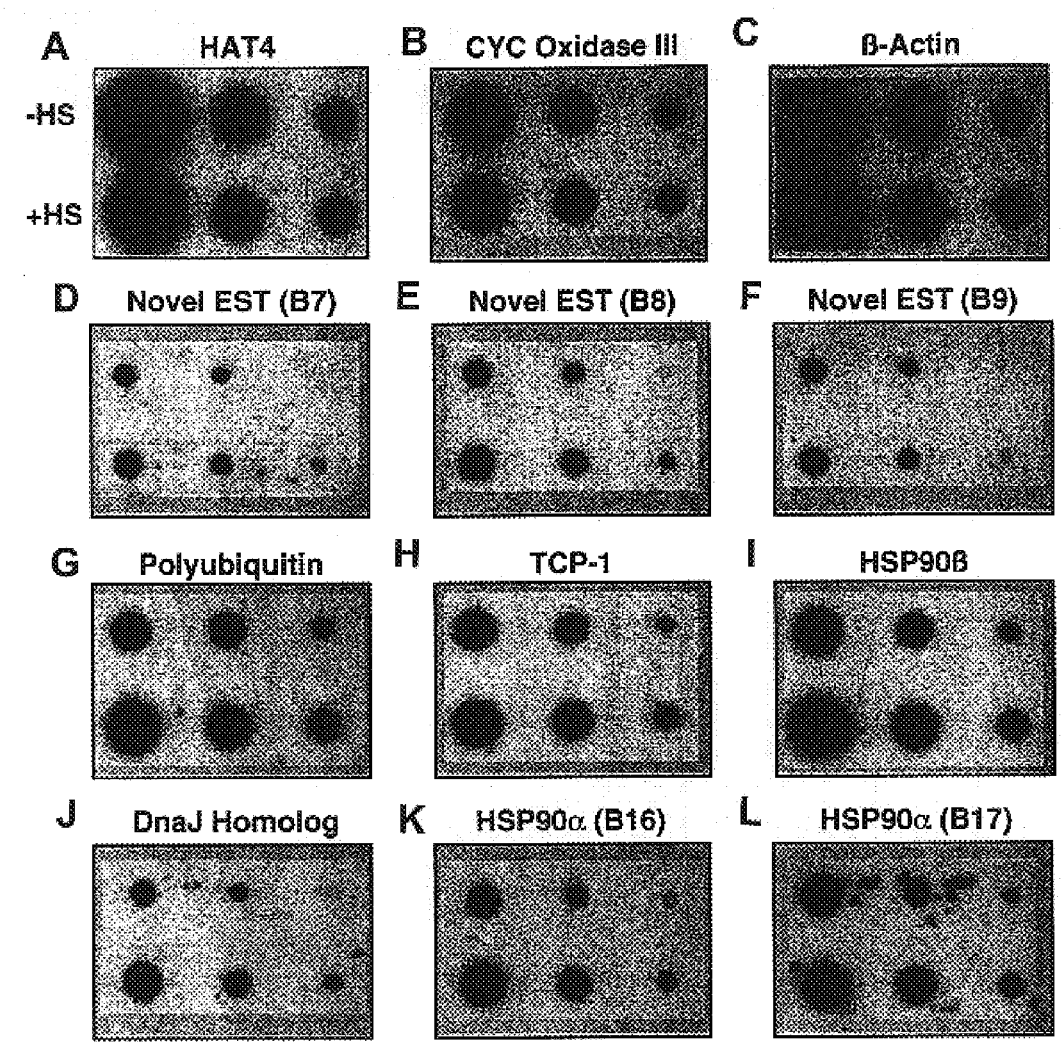
FIGS. 10A-10L are Northern RNA "dot" blots of samples of RNAs from control Jurkat cells (−HS) or heat-shocked Jurkat cells (+HS), after spotting onto nylon membranes, and blotting with the designated cDNA probes from Table 1.

To confirm that the changes in expression determined with the microarray assay corresponded to altered mRNA levels, each of the cloned sequences was used as a probe in RNA blotting analyses, as described in Example 3. All of the genes that displayed heat shock induction by microarray analysis yielded similar results in "dot blot" experiments (FIGS. 10A-10L and (Table 2, B1-B17). The gene encoding HSP90a, for example, exhibited 6.3-fold activation by microarray analysis and 7.2-fold induction by RNA blotting (FIG. 10I; Table 2). In all cases, expression ratios as determined by the two procedures differed by less than 2-fold for the genes identified in the heat shock experiments (Table 2). The two assays differed more widely in terms of assessing absolute expression levels; nonetheless, absolute expression as monitored on a microarray typically correlated with RNA blots to within a factor of five (Table 2).

TABLE 2

| | | Expression Level (per 105) | | | |
|---|---|---|---|---|---|
| Clone | Blast Identity | Microarray | Ratio | RNA Blot | Ratio |
| B1 | CYC oxidase III | 92/46 | 0.5 | 100/80 | 0.8 |
| B2 | β-Actin | 240/120 | 0.4 | 270/280 | 1.0 |
| B3 | CYC oxidase III | 36/18 | 0.5 | N.D. | N.D. |
| B4 | CYC oxidase III | 76/38 | 0.5 | N.D. | N.D. |
| B5 | CYC oxidase III | 62/31 | 0.5 | N.D. | N.D. |
| B6 | °-Actin | 180/89 | 0.5 | N.D. | N.D. |
| B7 | Novel (weakly to D76026) | 1.3/2.6 | 2.0 | 0.77/1.8 | 2.3 |
| B8 | Novel | 2.0/4.0 | 2.0 | 1.5/3.4 | 2.3 |
| B9 | Novel | 0.8/1.8 | 2.2 | 1.2/1.8 | 1.5 |
| B10 | Polyubiquitin | 0.8/72 | 2.4 | 25/89 | 3.6 |
| B11 | TCP-1 | 2.3/77 | 2.4 | 7.1/27 | 3.8 |
| B12 | Polyubiquitin | 0.8/2.0 | 2.5 | N.D. | N.D. |
| B13 | Polyubiquitin | 1.7/4.3 | 2.5 | N.D. | N.D. |
| B14 | HSP90° | 75/200 | 2.6 | 30/120 | 4.0 |

TABLE 2-continued

| | | Expression Level (per 105) | | | |
|---|---|---|---|---|---|
| Clone | Blast Identity | Microarray | Ratio | RNA Blot | Ratio |
| B15 | DnaJ homolog | 1.0/4.0 | 4.0 | 1.6/13 | 8.1 |
| B16 | HSP90a | 0.6/3.5 | 5.8 | 3.2/29 | 9.1 |
| B17 | HSP90a | 0.8/5.0 | 6.3 | 8.6/6.2 | 7.2 |

Genes that exhibited positive regulation in heat-treated T cells encode factors that either function as molecular "chaperones" of protein folding (HSP90α, HSP90β, DnaJ, TCP-1), or as mediators of selective protein degradation (polyubiquitin). The identification of these sequences is consistent the biochemical basis of heat shock induction. Many proteins undergo denaturation at elevated temperatures, and those that fail to maintain proper conformation must be selectively degraded (Jindal, 1996; Wilkinson, 1995; Jakob, et al., 1994; Becker and Craig, 1994; Cyr, 1994; Craig, et al., 1994). It will be interesting to determine whether the three novel heat shock-inducible sequences (B7-B9) identified in this study play a role in protein folding and turnover, or possess some other biochemical activity. Complete nucleotide sequence determination, conceptual translation, expression monitoring, and biochemical analysis should provide a clue to the function of these genes.

In summary, the method was successful in confirming a number of known heat-shock genes and identifying three new genes not previously associated with heat shock.

A third study was designed to identify genes whose level of expression is related to treatment with phorbol ester. Phorbol ester, a potent activator of the protein kinase C family (Newton, 1995; Nishizuka, 1995), activates a set of genes distinct from those involved in the heat shock pathway.

Control and phorbol-ester treated Jurkat cells were cultured as described in Example 4. Total cDNA from control and drug-treated cells was labeled by reverse transcriptase incorporation of fluorescein- or Cy5-derivatized dCTP, respectively, as detailed in Example 4. The two cDNA fractions were mixed and hybridized to the human PBL microarray above. The combined fluorescent scans for the two fluorophores are shown in FIG. 8.

Figures 9A, 9B:
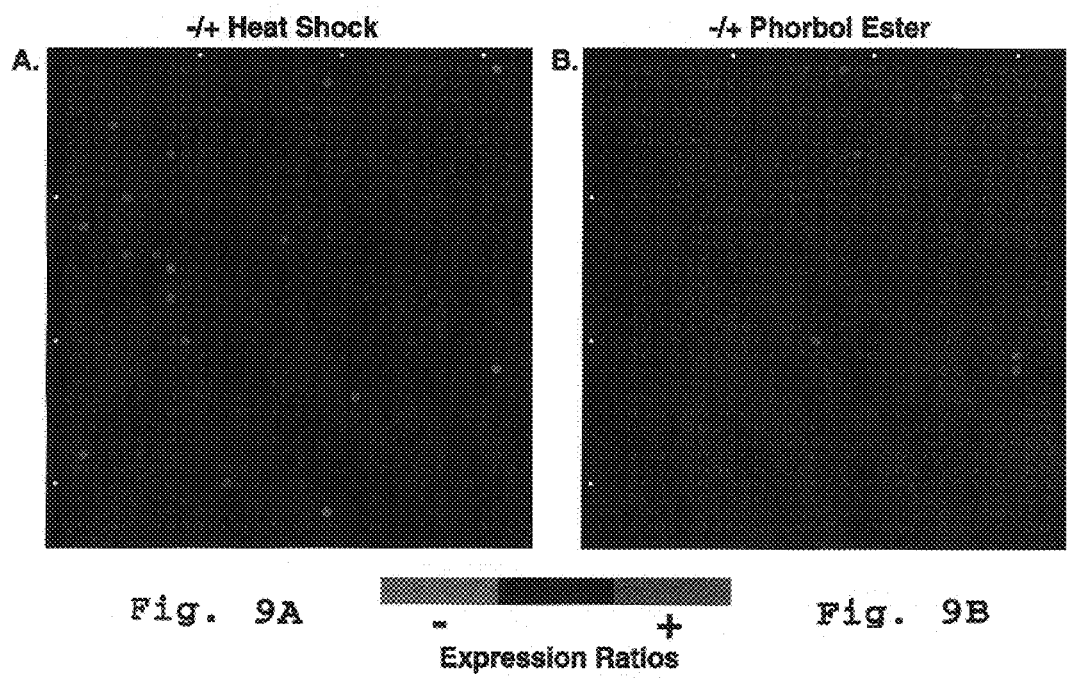
FIGS. 9A and 9B are schematic displays of activated and repressed genes in Jurkat cells in response to heat shock (9A) and phorbol ester (9B), where the colors indicated on the display correspond to array elements that display greater than 2-fold elevation (red), less than a 2-fold change (black), or less than 2-fold repression (green)

As above, examination of the fluorescent scans revealed positive hybridization signals to >95% of the human cDNA array elements, but not to any of the Arabidopsis controls. Hybridization intensities spanned more than three orders of magnitude for the 1,046 array elements surveyed. Comparative expression analysis of heat shocked versus control cells in the two experiments revealed altered fluorescence intensities at 6 array elements (Table 1 above, B18-B23), all of which showed modest to strong up-regulation in response to phorbol-ester treatment. The positions of the genes in the array are illustrated in FIG. 9B (red spots).

To determine the identity of the genes that exhibited altered expression patterns, cDNAs corresponding to each of the 6 array elements identified above were subjected to single pass DNA sequencing on the proximal end of each clone, as above. Database searches of the sequences revealed "hits" for 5 of the 6 clones (Table 1, B18-B23), including the two most highly induced genes (Table 1) which corresponded to a tyrosine phosphatase (PAC-1) (Rohan, et al., 1993) and nuclear factor-kappa B1 (NF-kB1) (Thanos, et al., 1995; Baeuerle, et al., 1994;

Liou, et al., 1993). Modest activation was also observed for genes encoding phosphoglycerate kinase (PGK), β-2-microglobulin, and one additional sequence (B19) that did not match any entry in the public database (Table 1).

Each of the phorbol ester-inducible genes identified by microarray analysis displayed increases in steady-state mRNA levels (FIGS. 11A-11E; Table 2, B18-23) in RNA blotting experiments.

It is striking that, despite the previous intensive analyses of both the heat shock and phorbol ester path-ways, 4 of the 15 sequences identified in the two studies above represent novel human genes. The fact that the four novel genes share the common features of relatively low expression (about 1:50,000) and modest activation (about 2.2-fold), suggests that these sequences may have been simply overlooked in screens utilizing prior-art differential techniques.

One way to examine the function of newly discovered genes is to determine their expression profiles in different tissues. To explore this, probes were prepared from human bone marrow, brain, prostate and heart by labeling mRNA with reverse transcriptase in the presence of Cy-5-dCTP. In a separate reaction, a control probe was prepared by labeling total Jurkat mRNA with fluorescein-dCTP. The four Cy-5-labeled tissue samples were each mixed with an aliquot of the fluorescein-labeled Jurkat probe, and the two-color probe mixtures were hybridized to four separate microarrays. The four arrays were then washed and scanned for fluorescence emission. Hybridization signals for each of the tissue samples were normalized internally to the Jurkat control and an expression profile was generated for each of the 1,046 genes represented on the array.

Figure 12:
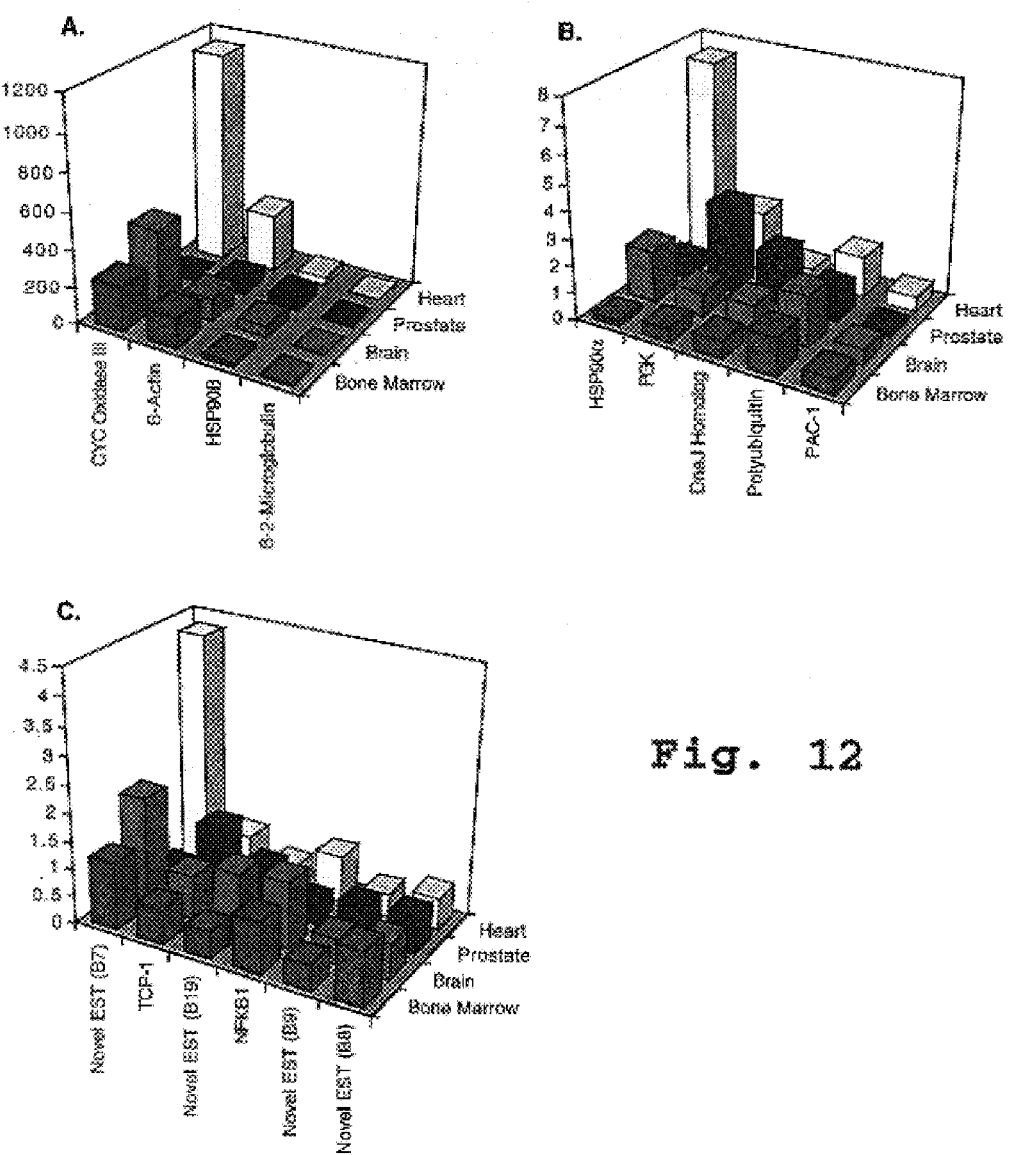
FIGS. 12A-12C show transcript profiles of heat shock- and phorbol ester-regulated genes, where gene expression levels per 10$^5$ mRNAs (x-axes) are shown for 15 genes (Table 1) in human bone marrow, brain, prostate, and heart, and the genes are grouped according to expression levels (A-C).

Detectable expression was observed for all 15 of the heat shock- and phorbol ester-regulated genes in the four tissue types examined. In general, the expression level of each gene in Jurkat cells correlated rather closely with expression in the four tissues. Genes encoding β-actin and cytochrome c oxidase, the two most highly expressed of the 15 genes in Jurkat cells (Table 2), were also highly expressed in bone marrow, brain, prostate, and heart (FIG. 12A); similarly, genes expressed at moderate or low levels in Jurkat cells (Table 2) displayed moderate to weak expression in the four tissue types (FIGS. 12B, 12C). One the novel heat shock genes (B7) showed an expression profile similar to the mitochondrial gene encoding CYC oxidase III.

From the foregoing, it can be appreciated how various objects and features of the method of the invention are met. The microarrays used in the experiment can be designed for probing a wide range of genes, e.g., from particular species, cell types, or cell states, and an array density which allows large numbers of genes, e.g., $10^5$-$10^6$ to be examined on a single array surface. This not only reduces the amount of work needed to screen large numbers of genes, but because a single array provides its own internal controls, allows higher resolution in determining relative levels of abundance of polynucleotide probe species on the array.

In the two-color, single-array mode, the method offers the additional advantage of an internal control in the levels of fluorescent signals associated with cDNA's obtained from two different sources. The greater resolution this features provides allows detection of differential gene expression, either up-regulation or down-regulation, of as low as 20%. As a result, it is possible not only to scan very large collections of gene transcripts on a single array, but also to detect relatively minor changes in gene expression in each array sequence. Another advantage of the two-color scheme is that even if the number of binding sites of the arrayed target DNA elements becomes limiting, the competitive hybridization of the two samples will saturate the sites in a ratio reflecting their relative abundance.

The studies involving genes' responses to heatshock or phorbol-ester treatment illustrate the ability of the method to rapidly identify new genes associated with such cell states.

The following examples illustrate, but in no way are intended to limit, the present invention.

V. General Methods

A. Microarray Preparation

Target messenger nucleic acid DNA fragments were prepared as described in the examples. In one general embodiment (DNA sequences non-covalently linked to microarray surface), the microarrays were fabricated on microscope slides which were coated with a layer of poly-l-lysine (Sigma). For each microarray region, an automated apparatus loaded 1 µl of the concentrated target DNA in 3× SSC directly from 96 well storage plates into the open capillary printing element and deposited about 5 nl of sample per slide at desired spacing between spots (Shalon, 1995), as described also in above-cited W095/35505.

After the spotting operation was complete, the slides were rehydrated in a humid chamber for 2 hours, baked in a dry 800° vacuum oven for 2 hours, rinsed to remove un-absorbed DNA and then treated with succinic anhydride to reduce non-specific adsorption of the labeled hybridization probe to the poly-l-lysine coated glass surface. Immediately prior to use, the immobilized DNA on the array was denatured in distilled water at 90° for 2 minutes.

In another general embodiment (DNA sequences convalently linked to the microarray surface), target sequences containing a reactive primary amine group on their 5' end were arrayed on a 1.0 cm² glass surface of a silylated microscope slides (CEL Associates), using the high-speed robotic printing method described above.

The target DNA sequences were linked covalently to the glass surface and heat denatured to allow hybridization. Briefly, the printed arrays were incubated for 4 hours in a humid chamber to allow rehydration of the array elements, rinsed once in 0.2% sodium dodecyl sulfate (SDS) for 1 min, twice in H₂O for 1 minute, and once in sodium borohydride solution (1.0 g $NaBH_4$ dissolved in 300 ml phosphate buffered saline (PBS) and 100 ml 100% ethanol). The arrays were submerged in $H_2O$ for 2 minute at 95° C., transferred quickly into 0.2% SDS for 1 minute, rinsed twice in $H_2O$, air dried, and stored in the dark at 25° C.

B. Preparation of Reporter-Labeled Messenger Nucleic Acid

Total RNA was isolated from a selected cell or tissue source using standard methods (Sambrook, et al., 1988). PolyA+ mRNA was prepared from total RNA using "OLIGOTEX-DT" resin (Qiagen). Reverse transcription reactions were carried out using a "STRATASCRIPT" RT-PCR kit (Stratagene) modified as follows: 50 µl reactions contained 0.1 µgl/µl mRNA, 0.1 ng/µl human acetylcholine receptor mRNA, 0.05 µg/µl oligo-dT (21mer), 1X first strand buffer, 0.03 units/µl RNase block, 500 µM DATP, 500 µM dGTP, 500 µM dTTP, 40 µM dCTP, 40 µM fluorescein-12-dCTP (or lissamine-5-dCTP) and 0.03 units/µl "STRATASCRIPT" reverse transcriptase. Reactions were incubated for 60 minutes at 37° C., precipitated with ethanol, and resuspended in 10 µl TE.

The samples were then heated for 3 minutes at 94° C. and chilled on ice. RNA was degraded by adding 0.25 µl 10N NaOH followed by a 10 min incubation at 37° C. The samples were neutralized by adding 2.5 µl 1M Tris-HCl (pH 8.0) and 0.25 µl 10N HCl, and precipitated with ethanol. Pellets were washed with 70% ethanol, dried to completion in a "SPEEDVAC" (Savant, Farmingdale, N.Y.) resuspended in 10 µl $H_2O$, and reduced to 3.0 μl in a SPEEDVAC. Fluorescent nucleotide analogs were purchased from DuPont NEN (Boston, Mass.).

C. Hybridization of Reporter-Labeled Nucleic Acid to Target DNA

Hybridization reactions contained 1.0 μl of fluorescent cDNA synthesis product (~2 μg) and 1.0 μl of hybridization buffer (10× SSC, 0.2% sodium dodecyl sulfate (SDS)). The 2.0 μl probe mixtures were aliquoted onto the microarray surface and covered with 12 mm round cover slips. Arrays were transferred to a waterproof slide chamber having a cavity just slightly larger than a microscope slide. The chamber was kept at 100% humidity internally by the addition of 2 microliters of water in a corner of the chamber. The chamber containing the arrays was incubated for 18 hours at 65° C.

The arrays were washed for 5 minutes at room temperature (25° C.) in low stringency wash buffer (1× SSC, 0.1% SDS), then for 10 minutes at room temperature in high stringency wash buffer (0.1× SSC, 0.1% SDS).

D. Detection of Hybridized Sequences

The microscope used to detect the reporter-labeled hybridization complexes was outfitted with an Innova 70 mixed gas 10 W laser (Coherent Lasers, Santa Clara, Calif.) capable of generating a number of spectral lines, including lines at 488 nm and 568 nm, and 632 nm (for Cy5). The excitation laser light was focused on the array using a 20× microscope objective (Nikon).

The-slide containing the array was placed on a computer-controlled X-Y stage on the microscope and raster-scanned past the objective. The 1.8 cm×1.8 cm array used in the present example was scanned with a resolution of 20 μm. Spatial resolutions up to a few micrometers are possible with appropriate optics.

In two separate scans, a mixed gas multiline laser excited the two fluorophores sequentially. Emitted light was split, based on wavelength, into two photomultiplier tube detectors (PMT R1477, Hamamatsu Photonics, San Jose, Calif.) corresponding to the two fluorophores. Appropriate filters positioned between the array and the photo-multiplier tubes were used to filter the signals. The emission maxima of the fluorophores used were 517 nm (fluorescein), 588 nm (lissamine), and 650 for Cy5. Each array was typically scanned twice—one scan per fluorophore, using the appropriate filters at the laser source —although the apparatus was capable of recording the spectra from both fluorophores simultaneously.

The sensitivity of the scans was typically calibrated using the signal intensity generated by an mRNA or cDNA control species added to the hybridization mix at a known concentration. For example, in the experiments described in Example 3, human acetylcholine receptor mRNA was added to the wild-type *Arabidopsis* poly-A total mRNA sample at a weight ratio of 1:10,000. A specific location on the array contained a complementary DNA sequence, allowing the intensity of the signal at that location to be correlated with a weight ratio of hybridizing species of 1:10,000.

When messenger nucleic acid-derived probes containing two different fluorophores (e.g., representing test and control cells) are hybridized to a single array for the purpose of identifying genes that are differentially expressed, a similar calibration scheme may be employed- to normalize the sensitivity of the photo-multiplier tubes such that genes expressed at the same levels in the test and control samples display the same pseudocolor intensity. In one embodiment, this calibration is done by labeling samples of the calibrating cDNA with the two fluorophores and adding identical amounts of each to the hybridization mixture.

It will be understood that where greater confidence in the absolute levels of expression is desired, multipoint calibrations may be performed.

E. Analysis of Patterns of Reporter Levels The output of the photomultiplier tube was digitized using a 12-bit RTI-835H analog-to-digital (A/D) conversion board (Analog Devices, Norwood, Mass.) installed in an IBM-compatible PC computer. The digitized data were displayed as an image where the signal intensity was mapped using a linear 20-color transformation to a pseudocolor scale ranging from blue (low signal) to red (high signal).

The data were also analyzed quantitatively. In cases where two different fluorophores were excited and measured simultaneously, the data were first corrected for optical crosstalk (due to overlapping emission spectra) between the fluorophores using each fluorophore's emission spectrum.

A grid was superimposed over the fluorescence signal image such that the signal from each spot was centered in each element of the grid. The fluorescence signal within each element was then integrated to obtain a numerical value corresponding to the average intensity of the signal. The software used for the above analyses was similar in functionality to "IMAGE-QUANT", available from Molecular Dynamics (Sunnyvale, Calif.).

EXAMPLE 1

Genomic-Complexity Hybridization to Micro DNA Arrays Representing the Yeast Saccharomyces Cerevisiae Genome with Two-Color Fluorescent Detection The array elements were randomly amplified PCR (Bohlander, et al., 1992) products using physically mapped lambda clones of *S. cerevisiae genomic* DNA templates (Riles, et al., 1993). The PCR was performed directly on the lambda phage lysates resulting in an amplification of both the 35 kb lambda vector and the 5-15 kb yeast insert sequences in the form of a uniform distribution of PCR product between 250-1500 base pairs in length. The PCR product was purified using Sephadex G50 gel filtration (Pharmacia, Piscataway, N.J.) and concentrated by evaporation to dryness at room temperature overnight. Each of the 864 amplified lambda clones was rehydrated in 15 μl of 3× SSC in preparation for spotting onto the glass.

The microarrays were fabricated on microscope slides coated with a layer of poly-l-lysine, as above. Immediately prior to use, the immobilized DNA on the array was denatured in distilled water at 900 for 2 minutes.

For the pooled chromosome experiment, the 16 chromosomes of Saccharomyces cerevisiae were separated in a CHEF agarose gel apparatus (Biorad, Richmond, Calif.). The six largest chromosomes were isolated in one gel slice and the smallest 10 chromosomes in a second gel slice. The DNA was recovered using a gel extraction kit (Qiagen, Chatsworth, Calif.). The two chromosome pools were randomly amplified in a manner similar to that used for the target lambda clones. Following amplification, 5 micrograms of each of the amplified chromosome pools were separately random-primer labeled using Klenow polymerase (Amersham, Arlington Heights, Ill.) with a lissamine conjugated nucleotide analog (Dupont NEN, Boston, Mass.) for the pool containing the six largest chromosomes, and with a fluorescein conjugated nucleotide analog (BMB) for the pool containing smallest ten chromosomes. The two pools were mixed and concentrated using an ultrafiltration device (Amicon, Danvers, Mass.).

Five micrograms of the hybridization probe consisting of both chromosome pools in 7.5 µl of TE was de-natured in a boiling water bath and then snap cooled on ice. 2.5 µl of concentrated hybridization solution was added (final concentration 5× SSC and 0.1% SDS), and all 10 µl transferred to the array surface, covered with a cover slip, placed in a custom-built single-slide humidity chamber and incubated at 60° for 12 hours. The slides were then rinsed at room temperature in 0.1× SSC and 0.1% SDS for 5 minutes, cover-slipped and scanned.

After correcting for optical crosstalk between the fluorophores due to their overlapping emission spectra, the red and green hybridization values for each clone on the array were correlated to the known physical map position of the clone resulting in a computer-generated color karyotype of the yeast genome, as shown in FIGS. 3A and 3B, discussed above.

EXAMPLE 2

Fluorescence Detection of Gene Expression Patterns using Micro Arrays of *Arabidopsis* cDNA Clones A. Microarray Preparation Target messenger nucleic acid DNA fragments were made by amplifying the gene inserts from 45 different *Arabidopsis thaliana* cDNA clones and 3 control genes using the polymerase chain reaction (PCR; Mullis, et al.). The DNA fragments comprising the PCR product from each of the 48 reactions were purified using "QIAQUICK" PCR purification kits (Qiagen, Chatsworth, Calif.), eluted in ddH$_2$O, dried to completion in a vacuum centrifuge and resuspended in 15 µl of 3×X sodium chloride/sodium citrate buffer (SSC). The capacity of the "QIAQUICK" purification kits is 10 µg of DNA; accordingly, each sample contained about 10 µg or less of DNA.

The samples were then deposited in individual wells of a 96 well storage plate with each sample split among two adjacent wells as a test of the reproducibility of the arraying and hybridization process. The samples were spotted on poly-l-lysine-coated microscope slides, as above, to produce a microarray with regions about 500 µm apart.

The positions of several specific elements in the 96-element array, and the reasons for their inclusion, are indicated in Table 3, below. The remaining elements of the array consist of known or unknown genes selected from an *Arabidopsis* cDNA library.

TABLE 3

| Element # | Name | Purpose |
|---|---|---|
| 1, 2 | Human acetylcholine receptor gene | Control for expression level |
| 13, 14 | Chlorophyll binding protein gene | Gene with known expression |
| 35, 36 | Rat glucocorticoid receptor gene | Positive and negative control |
| 49, 50 | HAT4 transcription factor gene | Gene with known expression |
| 95, 96 | Yeast TRP4 gene | Positive and negative control |

B. Methods

Total poly A+RNA was isolated from plant tissue of *Arabidopsis* using standard methods, and was used to prepare cDNA labeled with either fluorescein-12-dCTP or lissamine-5-dCTP, as above. Hybridization and scanning were carried out as above.

C. Two-Color Detection of Differential Gene Expression in Wild Type versus Transgenic *Arabidopsis* Tissue Differential gene expression was investigated using a simultaneous, two-color hybridization scheme, which served to minimize experimental variation inherent in comparing independent hybridizations. Two µg of wild-type *Arabidopsis* total cDNA that were labeled with fluorescein (as above) were combined with two micrograms of transgenic *Arabidopsis* total cDNA that were labeled by incorporating lissamine-5-dCTP (DuPont NEN) in the reverse transcription step and hybridized simultaneously to a microarray containing the same pattern of spotted cDNAs as described above.

To test whether overexpression of a single gene could be detected in a pool of total *Arabidopsis* mRNA, methods of the invention were used to analyze a transgenic line overexpressing the transcription factor HAT4 (Schena, et al., 1995). The transgenic *Arabidopsis* tissue was known to express HAT4 at levels of 0.5% of the total transcripts, while wild-type expression of HAT4 was only 0.01% of total transcripts (as previously determined by Northern analysis; Schena, et al., 1995).

Human acetylcholine receptor mRNA was added to the wild-type *Arabidopsis* poly-A total mRNA sample at a weight ratio of 1:10,000 and into the transgenic *Arabidopsis* poly-A total mRNA sample at a weight ratio of 1:100 to roughly match the expected expression levels of HAT4.

As a cross-check of the negative controls, linear PCR was used to generate single-stranded fluorescein-labeled rat glucocorticoid receptor DNA and lissamine-labeled yeast TRP4 DNA. The two PCR products were added to the hybridization solution at a partial concentration of ~1:100. The two fluorophores were excited separately in two separate scans in order to minimize optical crosstalk.

The array was then scanned separately for fluorescein and lissamine emission following independent excitation of the two fluorophores as described in Example 2, above. The results of the experiments are shown in FIGS. 4A and 4B.

D. Two-Color Detection of Differential Gene Expression in Root versus Leaf Tissue In a similar experiment using the same labeling and hybridization procedures described above, 2 µg of total cDNA from *Arabidopsis* root tissue labeled with fluorescein were combined with two micrograms of total cDNA from *Arabidopsis* leaf tissue labeled with lissamine and were simultaneously hybridized to a microarray containing the same pattern of target sequences described above. The acetylcholine receptor gene mRNA was added to both poly-A total mRNA samples at 1:1,000 to allow for normalization of fluorescence intensities. The glucocorticoid and TRP4 controls were added to the hybridization probe as before. The results are shown in FIGS. 5A and 5B.

EXAMPLE 3

Differential Gene Expression Due to Heat Shock in Human T cells (Jurkat Cell Line)

A. Constructing a Human Gene Expression Microarray

Human cDNA clones were picked at random from a human peripheral blood cDNA library, and propagated as bacterial cultures. The human cDNA library was made using mRNA isolated from human peripheral lymphocytes transformed with the Epstein-Barr Virus (EBV). Inserts of >600 bases were cloned into the lambda vector 1YES-R to generate 107-108 recombinants. Bacterial transformants were obtained by infecting *E. coli* strain JM107/lKC. Colonies were picked, propagated in a 96-well format, and minilysate DNA was prepared by alkaline lysis using REAL preps (Qiagen).

Plasmid DNA was isolated and inserts from each clone were amplified by use of the polymerase chain reaction (PCA) and purified. Inserts were amplified by PCR in a 96-well format using primers (PN132, 5'CCTCTATACTT-TAACGTCAAGG (SEQ ID NO.1); PAN133, 5'TTGTGTG-GAATTGTGAGCGG (SEQ ID NO.2)) complementary to the 1YES polylinker and containing a six carbon amino modification (Glen Research) on the 5'end. PCR products were purified in a 96-well format using QIAquick columns (Qiagen).

A total of 1,056 purified PCR inserts representing 1,046 human clones and 10 *Arabidopsis* controls were arrayed onto a 1.0 cm$^2$ glass surface of a glass slide, and attached covalently to the slide surface as detailed above.

B. Examining the Heat Shock Response in Human Cells

Human T (Jurkat) cells were grown in a tissue culture incubator (37° C. and 5% $CO_2$) in RMPI medium supplemented with 10% fetal bovine serum, 100 μg/ml streptomycin, and 500 μ/ml penicillin. The cells were propagated to near confluence under normal growth condition, divided into two equal aliquots, and grown for 4 hours at 37° C. and 43° C., respectively. Cells from the control (37° C.) and heat shocked culture (43° C.) were harvested, lysed (Ausubel, et al., 1994), and total mRNA from the two cell samples was labeled by reverse transcriptase incorporation of fluorescein- or Cy5-derivatized dCTP, respectively.

*Arabidopsis* control mRNAs were made by in vitro transcription of cloned HAT4, HAT22, and YesAt-23 cDNAs (Cohen, et al., 1995; Chan, et al., 1994; Crabtree, et al., 1994) using an RNA Transcription Kit (Stratagene). For quantitation, the mRNAs were doped into the RT reaction at ratios of 1:100,000, 1:10,000, and 1:1,000 (w/w) respectively.

Hybridizations and array scanning were carried out as above. To avoid complications arising from fluor-specific effects, the flours were "swapped" in a second set of labeling reactions, such that samples from control and heat shock-treated samples were labeled with Cy5- and fluorescein-dCTP, respectively. Each pair of fluorescent probes was mixed and hybridized to two 1,056 element human gene expression microarrays. The arrays were washed at high-stringency and scanned with a con-focal laser scanning device to detect emission of the two flours.

Examination of the fluorescent scans revealed positive hybridization signals to >95% of the human cDNA array elements, but not to any of the *Arabidopsis* controls. Hybridization intensities spanned more than three orders of magnitude for the 1,046 array elements surveyed. Comparative expression analysis of heat shocked versus control cells in the two experiments revealed altered fluorescence intensities at 17 array elements. Of the 17 putative differentially expressed genes, 11 were induced by heat shock treatment and 6 displayed modest repression.

C. Identification of Heat-Shock Related Genes

Sequencing reactions were carried out using the PAN132 and 133 primers and a 373A automated sequencer according to the instructions of the manufacturer (Applied Biosystems). Sequence searches were made to the non-redundant nucleotide database at the National Center for Biotechnology Information (NCBI) using Macintosh Blast software.

For dot-blot studies, samples of poly A+mRNA (9) corresponding to 1.0, 0.1 and 0.01 μg, respectively, were suspended in 10× SSC, spotted onto nylon membranes (Nytran), and crosslinked with ultraviolet light using a Stratalinker 1800 (Stratagene). Probes were prepared from cloned sequences (Table 1) by random priming using a Prime-It II kit (Stratagene) in the presence of $P^{32}$-dATP. Hybridizations were carried out following the instructions of the manufacturer. Quantitation was performed on a PhosphorImager (Molecular Dynamics).

EXAMPLE 4

Differential Gene Expression Due to Phorbol-Ester in Human T cells (Jurkat Cell Line)

To explore a signaling pathway distinct from the heat shock response, microarrays constructed as in Example 3 were used to examine the cellular effects of phorbol ester treatment. Jurkat cells were grown to near confluence, treated with phorbol ester, harvested, lysed and used as the source of mRNA, as above. Samples of mRNA from untreated or phorbol ester-stimulated cells were labeled by reverse transcriptase incorporation of fluorescent dCTP analogs, as above. The two-color fluorescent probes were mixed, hybridized to microarrays, and scanned for fluorescence emission. A total of six array elements displayed elevated fluorescent signals with probes derived from phorbol ester-treated cells relative to a controls (FIG. 8).

Although the invention has been described with respect to specific embodiments and methods, it will be clear that various changes and modification may be made without departing from the invention.

It is claimed:

1. A substrate with a surface consisting of a hydrophobic surface formed by the surface material or by a coating applied to the surface, comprising a microarray of DNA sequences, wherein (i) the microarray has a density of 1,000 or more discrete regions of DNA sequences per $cm^2$ of substrate surface, (ii) the DNA sequences are isolated polynucleotides, (iii) the microarray comprises 1,000 or more regions, and (iv) the DNA sequences contained in each discrete region are at least 50 subunits in length, which are individually applied to each region in the microarray, wherein each said region is formed by applying to said surface a volume of aqueous reagent solution comprising a DNA sequence selected for said region, wherein said hydrophobic surface prevents spreading of said volume applied to said surface via reagent bead formation.

2. The substrate of claim 1, wherein the density of discrete regions of DNA sequences is at least $2500/cm^2$.

3. The substrate of claim 1 or 2, wherein the substrate is glass.

4. The substrate of claim 1 or 2, wherein the substrate is non-porous.

5. The substrate of claim 1 or 2, wherein the DNA sequences are non-covalently bound to the surface of the substrate.

6. The substrate of claim 5, wherein the DNA sequences are non-covalently bound to a polycationic polymer on the surface of the substrate.

7. The substrate of claim 1 or 2, wherein the DNA sequences are selected from the group of polynucleotides consisting of mRNA-derived sequences, genomic DNA sequences and fragments thereof.

8. The substrate of claim 1 or 2, wherein the microarray comprises 2,500 or more regions.

9. A substrate with a surface consisting of a hydrophobic surface formed by the surface material or by a coating applied to the surface, comprising a microarray of DNA sequences, wherein the DNA sequences are polynucleotides of at least 50 subunits in length, produced by a method comprising the steps of (a) depositing a selected volume between about 0.002 nl and about 2 nl of a solution comprising a selected, isolated polynucleotide at a discrete region on the hydrophobic surface of the substrate, wherein said hydrophobic surface prevents spreading of said volume via reagent bead formation; and (b) repeating step (a) at other locations on the surface of the substrate until a microarray of 1,000 or more regions is formed, wherein the regions are at a density of at least $1,000 \text{ regions}/cm^2$.

10. The substrate of claim 9, wherein the density of discrete regions in the microarray is 2,500 $regions/cm^2$ or more.

11. The substrate of claim 9, wherein the substrate is glass.

12. The substrate of claim 9, wherein the substrate is non-porous.

13. The substrate of claim 9, wherein the DNA sequences are non-covalently bound to the surface of the substrate.

14. The substrate of claim 9, wherein the DNA sequences are selected from the group of polynucleotides consisting of mRNA-derived sequences, genomic DNA sequences, and fragments thereof.

15. The substrate of claim 9 or 10, wherein the microarray comprises 2,500 or more regions.

16. A substrate with a surface consisting of a hydrophobic surface formed by the surface material or by a coating applied to the surface, comprising a microarray of DNA sequences and suitable for analysis of a polynucleotide mixture, wherein (i) the microarray has a density of 1,000 or more discrete regions of DNA sequences per $cm^2$ of substrate surface (ii) each of said regions contains, as an isolated polynucleotide, a unique DNA sequence having at least 50 subunits, (iii) the microarray comprises at least 1,000 regions having individually applied DNA sequences unique to others of said 1,000 regions, such that the DNA sequences in said regions are selective in hybridizing with corresponding members of said mixture, wherein each said region is formed by applying to said surface a volume of aqueous reagent solution comprising a DNA sequence unique for said region, wherein said hydrophobic surface prevents spreading of said volume applied to said surface via reagent bead formation.

17. The substrate of claim 16, wherein the microarray permits detection of a two-fold change in the relative abundance of polynucleotides in mixtures subjected to analysis.

18. A substrate with a surface consisting of a hydrophobic surface formed by the surface material or by a coating applied to the surface, comprising a microarray of DNA sequences where (i) the microarray has a density of 1,000 or more discrete regions of DNA sequences per $cm^2$ of substrate surface, (ii) the DNA sequences are purified polynucleotides having at least 50 subunits, and (iii) the DNA sequences are non-covalently bound to a polycationic polymer on the surface of the substrate, wherein each said region is formed by applying to said surface a volume of aqueous reagent solution comprising a DNA sequence unique for said region, wherein said hydrophobic surface prevents spreading of said volume applied to said surface via reagent bead formation.

19. The substrate according to claim 18, wherein the DNA sequences are cDNAs.

20. The substrate of claim 1, 9, 16 or 18, wherein the DNA sequences are distinct gene sequences whose expression levels are specifically related to the differences between test cells relative to control cells.

* * * * *

UNITED STATES PATENT AND TRADEMARK OFFICE
CERTIFICATE OF CORRECTION

PATENT NO. : 7,442,499 B2 Page 1 of 1
APPLICATION NO. : 09/356322
DATED : October 28, 2008
INVENTOR(S) : Brown et al.

It is certified that error appears in the above-identified patent and that said Letters Patent is hereby corrected as shown below:

Column 1, lines 19-21, delete "The United States government may have certain rights in the present invention pursuant to Grant No. HG00450 by the National Institutes of Health." and insert --This invention was made with Government support under contract HL002668 awarded by the National Institutes of Health. The Government has certain rights in this invention.--

Signed and Sealed this

Thirty-first Day of August, 2010

David J. Kappos
*Director of the United States Patent and Trademark Office*